United States Patent
Coulter et al.

(10) Patent No.: US 8,334,317 B2
(45) Date of Patent: Dec. 18, 2012

(54) CALCIUM RECEPTOR MODULATING AGENTS

(75) Inventors: Thomas S. Coulter, Wantage (GB); Christopher H. Fotsch, Thousand Oaks, CA (US); Chiara Ghiron, Siena (IT); Paul E. Harrington, Camarillo, CA (US); Michael G. Kelly, Thousand Oaks, CA (US); Philip Miller, Reading (GB); Gilbert M. Rishton, Malibu, CA (US); David J. St. Jean, Jr., Camarillo, CA (US); David J. Semin, Thousand Oaks, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 12/738,279

(22) PCT Filed: Oct. 15, 2008
(Under 37 CFR 1.47)

(86) PCT No.: PCT/US2008/011755
§ 371 (c)(1),
(2), (4) Date: Dec. 10, 2010

(87) PCT Pub. No.: WO2009/051718
PCT Pub. Date: Apr. 23, 2009

(65) Prior Publication Data
US 2011/0178133 A1 Jul. 21, 2011

Related U.S. Application Data

(60) Provisional application No. 60/998,933, filed on Oct. 15, 2007.

(51) Int. Cl.
*A61K 31/41* (2006.01)
*A61K 31/4439* (2006.01)
*C07D 401/12* (2006.01)

(52) U.S. Cl. ........ 514/444; 514/469; 514/503; 514/509; 548/410; 548/411; 548/412; 548/415

(58) Field of Classification Search .................. 514/410, 514/411, 412, 415; 548/444, 469, 503, 509
See application file for complete search history.

(56) References Cited

U.S. PATENT DOCUMENTS

| | | | |
|---|---|---|---|
| 6,011,068 A | 1/2000 | Nemeth et al. | |
| 6,031,003 A | 2/2000 | Nemeth et al. | |
| 6,313,146 B1 | 11/2001 | Van Wagenen et al. | |
| 6,403,832 B1 | 6/2002 | Oikawa et al. | |
| 6,407,111 B1 | 6/2002 | Bos et al. | |
| 6,436,152 B1 | 8/2002 | Chassot et al. | |
| 6,894,190 B2 | 5/2005 | Oikawa et al. | |
| 6,908,935 B2 | 6/2005 | Kelly et al. | |
| 7,084,167 B2 | 8/2006 | Ruat et al. | |
| 7,157,498 B2 | 1/2007 | Dauban et al. | |
| 7,176,322 B2 * | 2/2007 | Kelly et al. | 548/469 |
| 2007/0225296 A1 | 9/2007 | Miyazaki et al. | |

FOREIGN PATENT DOCUMENTS

| | | | |
|---|---|---|---|
| EP | 1757582 A | | 2/2007 |
| EP | 1882684 A | | 1/2008 |
| JP | 2002030050 | | 1/2002 |
| WO | WO 97/41090 | * | 11/1997 |
| WO | WO 97/41090 | | 11/1997 |
| WO | WO 2004/030669 A | | 4/2004 |
| WO | WO 2005/115975 A | | 12/2005 |
| WO | WO 2006/123725 A | | 11/2006 |
| WO | WO 2008/035381 | | 3/2008 |

OTHER PUBLICATIONS

Brown et al., "Neomycin mimics the effects of high extracellular calcium concentrations on paratyhroid function in dispersed bovine parathyroid cells," Endocrinology, vol. 128, No. 6, 3047-3054, 1991.
Chen et al., "The diltiazem analog TA-3090 mimics the actions of high extracellular Ca2+ on parathyroid function in dispersed bovien parathyroid cells," Journal of Bone and Mineral Research, vol. 5, No. 6, 581-587, 1990.
Dauban et al., "N1-Arylsulfonyl-N2-(1-aryl)ethyl-3-phenylpropane-1,2-diamines as novel calcimimetics acting on the calcium sensing receptor," Biorg. Med. Chem, Lett. 10, 2001-2004, 2000.
Didiuek et al., "Short-acting 5-(trifluoromethyl)pyridol[4,3-d]pyrimidin-4(3H)-one derivatives as orally-active calcium-sensing receptor antagonists," Biorg, Med. Chem. Lett., 19, 4555-4559, 2009.
Garrett et al., "Calcitonin-secreting cells of the thyroid express an extracellular calcium receptor gene," Endocrinology, vol. 136, No. 11, 5202-5211, 1995.
Garrett et al., "Molecular cloning and functional expression of human parathyroid calcium receptor cDNAs," Journal of Biological Chemistry, vol. 270, No. 21, 12919-12925, 1995.
Nemeth et al., "Regulation of cytosolic calcium by extracellulary divalent cations in c-cells and parathyroid cells," Cell Calcium, vol. 11, 323-327, 1990.
Nemeth et al., "Calcimimetics with potent and selective activity on the parathyroid calcium receptor," Pharmacology, vol. 95, 4040-4045, Mar. 1998.
Svensson et al., "The design and bolactivation of presystematically stable prodrugs," Drug Metabolism Reviews, 19(2), 165-194, 1988.

(Continued)

*Primary Examiner* — Susannah Chung
(74) *Attorney, Agent, or Firm* — Olga Mekhovich

(57) ABSTRACT

The present invention relates generally to novel calcimimetic compounds and pharmaceutical compositions comprising them. The invention also relates to methods of treating of diseases or disorders related to the function of the calcium sensing receptor using the compounds represented in Formula I.

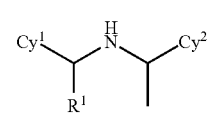

I

3 Claims, No Drawings

OTHER PUBLICATIONS

Zaidi et al., "Intracellular calcium in the control of osteoclast function," Biochemical and Biophysical Research Communications, vol. 167, No. 2, 807-812, Mar. 16, 1990.

Zaidi et al., "Calcium receptors on eukaryotic cells with special reference to the osteoclast," Bioscience Reports, vol. 10, No. 6, 493-507, 1990.

* cited by examiner

CALCIUM RECEPTOR MODULATING AGENTS

CROSS REFERENCE TO RELATED APPLICATIONS

This application claims priority to U.S. Provisional Application Ser. No. 60/998,933 filed Oct. 15, 2007, the entirety of which is incorporated herein by reference.

FIELD OF THE INVENTION

This invention relates generally to the field of medicine and, more specifically, to calcium receptor modulating compounds and pharmaceutical compositions comprising them.

BACKGROUND OF THE INVENTION

Extracellular calcium ion concentration is involved in a variety of biological processes, such as blood clotting, nerve and muscle excitability and bone formation (Cell Calcium 11:319, 1990). One of the key elements of this regulation is the calcium receptor known as the Ca sensing receptor or CaSR. Calcium ion receptors, which are present on the membranes of various cells in the body, such as parathyroid and kidney cells (Nature 366:574, 1993; J. Bone Miner. Res. 9, Supple. 1, s282, 1994; J. Bone Miner. Res. 9, Supple. 1, s409, 1994; Endocrinology 136:5202, 1995), are important to the regulation of the extracellular calcium ion concentration. For example, concentration of extracellular calcium ion regulates the bone resorption by osteoclasts (Bioscience Reports 10:493, 1990), secretion of parathyroid hormone (PTH) from parathyroid cells and secretion of calcitonin from C-cells (Cell Calcium 11:323, 1990). Parathyroid cells thus have at their surface the calcium sensing receptor (CaSR), which detects changes in extracellular calcium concentration and initiates the functional response of this cell, which is a modulation of the secretion of the parathyroid hormone (PTH). Secretion of PTH increases extracellular calcium ion concentration by acting on various cells, such as bone and kidney cells, and the extracellular calcium ion concentration reciprocally inhibits the secretion of PTH by acting on parathyroid cells. The reciprocal relationship between calcium concentration and PTH level is an essential mechanism for calcium homeostasis maintenance.

The cloning of the calcium receptor by Brown in 1993 consequently demonstrated two possible signalling pathways for this G protein coupled receptor: one pathway by activation of the Gi protein (sensitive to the pertussis toxin) which stimulates phospholipase C and inhibits adenylate cyclase; the other pathway by activating the Gq protein responsible for mobilising intracellular calcium. These two signalling pathways, either independently of one another or together, can be activated so as to trigger the associated biological effect. On its extracellular portion, the calcium receptor is a low affinity receptor which is stimulated by millimolar concentrations of agonists, in particular the calcium ion $Ca^{2+}$. In addition, this receptor can also be activated by some divalent metals (magnesium) or trivalent metals (gadolinium, lanthanum, etc.) or else by polycationic compounds such as neomycin or spermine.

Several classes of calcimimetic compounds have been disclosed for regulating extracellular calcium ion concentration, particularly for reducing or inhibiting secretion of PTH. For example, U.S. Pat. Nos. 6,011,068 and 5,981,599 disclose arylalkylamines that are calcium receptor active molecules. EP 933354; WO 0021910, WO 96/12697; WO 95/11221; WO 94/18959; WO 93/04373; WO 06/123725, AU 2004202208, Endocrinology 128:3047, 1991; Biochem. Biophys. Res. Commun. 167:807, 1990; J. Bone Miner. Res. 5:581, 1990; and Nemeth et al., "Calcium-binding Proteins in Health and Disease," Academic Press, Inc., pp. 33-35 (1987) disclose various agents that interact with calcium receptors.

Dauban et al., Bioorg. Med. Chem. Let. 10:2001-4, 2000, disclose various N1-arylsulfonyl-N2-(1-aryl)ethyl-3-phenyl-propane-1,2-diamine compounds as calcimimetics acting on the calcium sensing receptor.

Oikawa et al., in U.S. Pat. No. 6,403,832, and publication No. US2002/143212, describes aryl amine compounds useful as chiral intermediates in the synthesis of optically active propionic acid derivatives. Chassot et al., U.S. Pat. No. 6,436,152, describes arylalkylamine compounds useful as hair dye precursor compounds. Other calcimimetic compounds are disclosed in U.S. Pat. Nos. 6,313,146; 6,001,884; PCT publications WO 01/34562; WO 01/90069; WO 02/059102; WO 02/12181; WO 05/115975; WO 06/117211; WO 06/123725; WO 08/059,854; WO 08/019,690.

SUMMARY OF THE INVENTION

The present invention relates to selected calcimimetic compounds and pharmaceutically acceptable salts thereof. This invention also encompasses pharmaceutical compositions, methods for reducing or inhibiting PTH secretion and methods for treatment or prophylaxis of diseases associated with excessive secretion of PTH, such as hyperparathyroidism. Thus, in one aspect, the invention compounds advantageously reduce or inhibit PTH secretion. In another aspect, the compounds of the invention are useful for treatment of other diseases and disorders associated with the function of the calcium sensing receptor, such as vascular calcification, polycystic kidney disease, podocyte-related disorders and inflammatory bowel disorders.

In one aspect, the invention provides compounds or pharmaceutically acceptable salts thereof, wherein the compounds are selected from the group consisting of:

(1R)—N-(1H-imidazol-5-ylmethyl)-1-(1-naphthyl)ethanamine, (1R)-1-(3-methoxyphenyl)-N-[(1-methyl-1H-pyrrol-2-yl)methyl]ethanamine, (1R)—N-[(1-methyl-1H-pyrrol-2-yl)methyl]-1-(1-naphthyl)ethanamine, (1R)-1-(1-naphthyl)-N-(1H-pyrrol-2-ylmethyl)ethanamine, (1R)-1-(3-methoxyphenyl)-N-{[1-(phenylsulfonyl)-1H-pyrrol-2-yl]methyl}ethanamine, (1R)-1-(1-naphthyl)-N-{[1-(phenyl sulfonyl)-1H-pyrrol-2-yl]methyl}ethanamine, (1R)-1-(3-methoxyphenyl)-N-(1H-pyrrol-2-ylmethyl)ethanamine, (1R)-1-(3-methoxyphenyl)-N-(1,3-thiazol-2-ylmethyl)ethanamine, (1R)—N-((4-chloro-1-methyl-1H-pyrazol-3-yl)methyl)-1-(3-(methyloxy)phenyl)ethanamine, (1R)—N-((4-chloro-1-methyl-1H-pyrazol-3-yl)methyl)-1-(1-naphthalenyl)ethanamine, (1R)-1-(3-(methyloxy)phenyl)-N-((2-phenyl-1H-imidazol-4-yl)methyl)ethanamine, (1R)-1-(1-naphthalenyl)-N-((2-phenyl-1H-imidazol-4-yl)methyl)ethanamine, (1R)-1-phenyl-N-((2-phenyl-1H-imidazol-4-yl)methyl)ethanamine, (1R)—N-((3,5-dimethyl-1-phenyl-1H-pyrazol-4-yl)methyl)-1-(3-(methyloxy)phenyl)ethanamine, (1R)—N-((3,5-dimethyl-1-phenyl-1H-pyrazol-4-yl)methyl)-1-(4-methylphenyl)ethanamine,
(1R)—N-((3,5-dimethyl-1-phenyl-1H-pyrazol-4-yl)methyl)-1-(1-naphthalenyl)ethanamine,
(1R)—N-((3,5-dimethyl-1-phenyl-1H-pyrazol-4-yl)methyl)-1-phenylethanamine,
(1R)-1-(4-(methyloxy)phenyl)-N-((5-methyl-3-phenyl-4-isoxazolyl)methyl)ethanamine,
(1R)—N-((5-methyl-3-phenyl-4-isoxazolyl)methyl)-1-(1-naphthalenyl)ethanamine,
(1R)—N-((5-methyl-3-phenyl-4-isoxazolyl)methyl)-1-phenylethanamine,
(1R)-1-(3-(methyloxy)phenyl)-N-((3-phenyl-1H-pyrazol-4-yl)methyl)ethanamine,
(1R)-1-(4-(methyloxy)phenyl)-N-((3-phenyl-1H-pyrazol-4-yl)methyl)ethanamine,
(1R)-1-(1-naphthalenyl)-N-((3-phenyl-1H-pyrazol-4-yl)methyl)ethanamine,
(1R)-1-phenyl-N-((3-phenyl-1H-pyrazol-4-yl)methyl)ethanamine,
(1R)—N-(1H-imidazol-2-ylmethyl)-1-(4-methylphenyl)ethanamine,
(1R)—N-(1H-imidazol-2-ylmethyl)-1-(1-naphthalenyl)ethanamine,
(1R)—N-((2-ethyl-4-methyl-1H-imidazol-5-yl)methyl)-1-(1-naphthalenyl)ethanamine,
(1R)—N-((2-(4-chlorophenyl)-1,3-thiazol-4-yl)methyl)-1-(4-methylphenyl)ethanamine,
(1R)—N-((2-(4-chlorophenyl)-1,3-thiazol-4-yl)methyl)-1-(1-naphthalenyl)ethanamine,
(1R)—N-((2-(4-chlorophenyl)-1,3-thiazol-4-yl)methyl)-1-(2-naphthalenyl)ethanamine,
(1R)-1-(1-naphthalenyl)-N-((2-phenyl-1,3-thiazol-4-yl)methyl)ethanamine,
(1R)—N-((3-(4-(1,1-dimethylethyl)phenyl)-1,2,4-oxadiazol-5-yl)methyl)-1-(4-methylphenyl)ethanamine,
(1R)—N-((3-(4-(1,1-dimethylethyl)phenyl)-1,2,4-oxadiazol-5-yl)methyl)-1-(2-naphthalenyl)ethanamine,
(1R)-1-(1-naphthalenyl)-N-((1-phenyl-1H-pyrazol-5-yl)methyl)ethanamine,
1-(4-fluorophenyl)-4-({[(1R)-1-(1-naphthyl)ethyl]amino}methyl)pyrrolidin-2-one,
4-({[(1R)-1-(3-chlorophenyl)ethyl]amino}methyl)-1-(4-fluorophenyl)pyrrolidin-2-one,
(1R)—N-[(5-chloro-1-methyl-4-phenyl-1H-imidazol-2-yl)methyl]-1-phenylethanamine,
(1R)-1-phenyl-N-[(2-phenyl-1,3-thiazol-4-yl)methyl]ethanamine,
(1R)-1-(3-chlorophenyl)-N-{[1-(4-fluorophenyl)pyrrolidin-3-yl]methyl}ethanamine,
(1R)-1-(1-naphthyl)-N-({1-[4-(trifluoromethyl)phenyl]-1H-pyrazol-3-yl}methyl)ethanamine,
(1R)-1-(3-fluorophenyl)-N-({1-[4-(trifluoromethyl)phenyl]-1H-pyrazol-3-yl}methyl)ethanamine,
(1R)-1-(3-chlorophenyl)-N-({1-[4-(trifluoromethyl)phenyl]-1H-pyrazol-3-yl}methyl)ethanamine,
(1R)—N-({5-methoxy-1-[4-(tri)phenyl]-1H-pyrazol-3-yl}methyl)-1-phenylethanamine,
(1R)-1-(3-fluorophenyl)-N-({5-methoxy-1-[4-(trifluoromethyl)phenyl]-1H-pyrazol-3-yl}methyl)ethanamine,
(1R)-1-(3-chlorophenyl)-N-({5-methoxy-1-[4-(trifluoromethyl)phenyl]-1H-pyrazol-3-yl}methyl)ethanamine,
1-{5-methoxy-1-[4-(trifluoromethyl)phenyl]-1H-pyrazol-3-yl}-N-[(1R)-1-phenylethyl]ethanamine,
(1R)-1-(3-fluorophenyl)-N-(1-{5-methoxy-1-[4-(trifluoromethyl)phenyl]-1H-pyrazol-3-yl}ethyl)ethanamine,
(1R)-1-(3-chlorophenyl)-N-{1-[1-(3-chlorophenyl)-5-methoxy-1H-pyrazol-3-yl]ethyl}ethanamine,
1-[1-(3-chlorophenyl)-5-methoxy-1H-pyrazol-3-yl]-N-[(1R)-1-(3-fluorophenyl)ethyl]ethanamine,
1-(1-(3-chlorophenyl)-5-methoxy-1H-pyrazol-3-yl)-N-[(1R)-1-phenylethyl]ethanamine,
(1R)-1-(3-chlorophenyl)-N-(1-{5-methoxy-1-[4-(tri)phenyl]-1H-pyrazol-3-yl}ethyl)ethanamine,
1-[1-(4-bromophenyl)-5-methoxy-1H-pyrazol-3-yl]-N—[(1R)-1-(3-chlorophenyl)ethyl]ethanamine,
4-[3-(1-{[(1R)-1-(3-chlorophenyl)ethyl]amino}ethyl)-5-methoxy-1H-pyrazol-1-yl]benzonitrile,
1-{5-methoxy-1-[6-(trifluoromethyl)pyridin-3-yl]-1H-pyrazol-3-yl}-N-[(1R)-1-phenylethyl]ethanamine,
(1R)-1-(3-fluorophenyl)-N-(1-(5-methoxy-1-[6-(trifluoromethyl)pyridin-3-yl)-1H-pyrazol-3-yl)ethyl)ethanamine,
(1R)-1-(3-chlorophenyl)-N-(1-{5-methoxy-1-[6-(trifluoromethyl)pyridine-3-yl]-1H-pyrazol-3-yl)ethyl)ethanamine,
(1R)-1-phenyl-N-(1-{1 [4-(trifluoromethyl)phenyl]-1H-pyrazol-3-yl}ethyl)ethanamine,
(1R)-1-(3-fluorophenyl)-N-(1-{1-[4-(trifluoromethyl)phenyl]-1H-pyrazol-3-yl}ethyl)ethanamine,
2-methyl-N-[(1R)-1-phenylethyl]-1-{1-[4-(trifluoromethyl)phenyl]-1H-pyrazol-3-yl}propan-1-amine,
(1R)-1-(3-chlorophenyl)-N-((1R)-1-(1-(4-(trifluoromethyl)phenyl)-1H-pyrazol-3-yl)ethyl)ethanamine, and
N-[(1R)-1-phenylethyl]-1-{1 [4-(trifluoromethyl)-1H-pyrazol-3-yl}propan-1-amine,
or a pharmaceutically acceptable salt thereof.

In another aspect, the invention provides methods for treating a patient in need of such treatment comprising the step of administering to the patient a therapeutically effective amount of a compound of Formula I

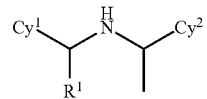

I or a pharmaceutically acceptable salt thereof, wherein all substituents are as described in Detailed Description below.

In one aspect, the patient has a disease characterized by abnormal calcium homeostasis. In one aspect, the disease is hyperparathyroidism. In another aspect, the disease is vascular calcification. In a further aspect, the disease can be a polycystic kidney disorder. In another aspect, the disease can be an abnormal intestinal motility, such as diarrhea. In a further aspect, the disease may be a podocyte-related disorder. In one aspect, the disease or disorder can be malassimilation or malnutrition. In another aspect, the disease can be IBD or IBS.

The invention also provides pharmaceutical compositions comprising the compounds of the invention or a pharmaceutically acceptable salt thereof and a pharmaceutically acceptable diluent or carrier.

DETAILED DESCRIPTION OF THE INVENTION

I. Definitions

"Treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase "therapeutically effective amount" is the amount of the compound of the invention that will achieve the goal of prevention of the disorder or improvement in disorder severity and the frequency of incidence. The improvement in disorder severity includes the reversal of the disease, as well as slowing down the progression of the disease.

As used herein, "calcium sensing receptor" or "CaSR" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., *Adv Pharmacol* 47: 209-253, 2000).

Unless otherwise specified, the following definitions apply to terms found in the specification and claims:

The term "alkyl" by itself or as part of another substituent, means, unless otherwise stated, a straight or branched chain, or cyclic, saturated hydrocarbon having the indicated number of carbon atoms (i.e., $C_1$-$C_8$ means one to eight carbons). For example, ($C_1$-$C_8$) alkyl is meant to include, but is not limited to methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl.

The term "alkenyl" as used herein refers to a straight or branched chain unsaturated hydrocarbon having the indicated number of carbon atoms (i.e., $C_2$-$C_8$ means two to eight carbons) and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene.

The term "alkylene" refers to a divalent alkyl group (e.g., an alkyl group attached to two other moieties, typically as a linking group). Examples of a ($C_1$-$C_8$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, $CH_2CH_2CH_2CH_2CH_2CH_2$—, and —$CH_2CH_2CH_2CH_2CH_2CH_2CH_2$—, as well as branched versions thereof. The term "alkenylene" refers to a divalent alkenyl group (e.g., an alkenyl group attached to two other moieties, typically as a linking group). Examples of a ($C_2$-$C_8$) alkenylene group include —CH=CH—, —$CH_2$CH=CH—, —$CH_2$CH=CH$CH_2$—, as well as branched versions thereof.

Typically, an alkyl, alkenyl, alkylene, or alkenylene group will have from 1 to 24 carbon atoms, with those groups having 10 or fewer carbon atoms being preferred in the present invention. A "lower alkyl" "lower alkenyl" or "lower alkylene" is a shorter chain alkyl or alkylene group, generally having eight or fewer carbon atoms.

The term "heteroatom" is meant to include oxygen (O), nitrogen (N), sulfur (S) and silicon (Si).

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The term "aryl" as used herein refers to a 6- to 14-membered monocyclic, bicyclic or tricyclic aromatic hydrocarbon ring system. Examples of an aryl group include phenyl and naphthyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl. A heteroaryl group can be unsubstituted or optionally substituted with one or more substituents as described herein below.

The term "heterocycle", "heterocyclic residue" or "heterocyclyl" as used herein refer to 3- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls, heterocycloalkyls, and heterocycloalkenyls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "alkoxy" as used herein refers to an —O-alkyl group. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl. The term "alkoxyalkyl" refers to an alkoxy group appended to an alkyl radical. The term "aryloxy" as used herein refers to an —O-aryl group. The term "alkoxyaryl" refers to an alkoxy group attached to an aryl radical.

The term "amino" refers to a chemical functionality —NR'R", wherein R' and R' are independently hydrogen, alkyl or aryl.

The term "halo" or "halogen" as used herein refers to —F, —Cl, —Br or —I.

The term "haloalkyl," as used herein, refers to a $C_1$-$C_6$ alkyl group wherein one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2 m'+1) halogen atoms, where m' is the total number of carbon atoms in the alkyl group).

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3$^{rd}$ Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses calcium-sensing receptor modulators and their uses as described herein in the form of their optical isomers, and mixtures thereof, including a racemic mixture. Optical isomers of the calcium-sensing receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, e.g., cancer therapeutic agents, research reagents, e.g., assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

II. Compounds that Modulate Calcium Sensing Receptor and Pharmaceutical Compositions Comprising them, Administration and Dosage As used herein, the term "calcimimetic compound" or "calcimimetic" refers to a compound that binds to calcium sensing receptors and induces a conformational change that reduces the threshold for calcium sensing receptor activation by the endogenous ligand $Ca^{2+}$. These calcimimetic compounds can also be considered allosteric modulators of the calcium receptors.

In one aspect, a calcimimetic can have one or more of the following activities: it evokes a transient increase in internal calcium, having a duration of less than 30 seconds (for example, by mobilizing internal calcium); it evokes a rapid increase in $[Ca^{2+}]_i$ occurring within thirty seconds; it evokes a sustained increase (greater than thirty seconds) in $[Ca^{2+}]_i$ (for example, by causing an influx of external calcium); evokes an increase in inositol-1,4,5-triphosphate or diacylglycerol levels, usually within less than 60 seconds; and inhibits dopamine- or isoproterenol-stimulated cyclic AMP formation. In one aspect, the transient increase in $[Ca^{2+}]_i$ can be abolished by pretreatment of the cell for ten minutes with 10 mM sodium fluoride or with an inhibitor of phospholipase C, or the transient increase is diminished by brief pretreatment (not more than ten minutes) of the cell with an activator of protein kinase C, for example, phorbol myristate acetate (PMA), mezerein or (−) indolactam V.

While the compounds of the invention are believed to exert their effects by interacting with the calcium sensing receptor (CaSR), the mechanism of action by which the compounds act is not a limiting embodiment of the invention. For example, compounds of the invention may interact with calcium sensing receptors other than CaSR.

Compounds contemplated by the invention include, but are not limited to, the exemplary compounds provided herein.

In certain embodiments, the calcimimetic compound is chosen from the following compounds or pharmaceutically acceptable salts thereof:
(1R)—N-(1H-imidazol-5-ylmethyl)-1-(1-naphthyl)ethanamine,
(1R)-1-(3-methoxyphenyl)-N-[(1-methyl-1H-pyrrol-2-yl)methyl]ethanamine,
(1R)—N-[(1-methyl-1H-pyrrol-2-yl)methyl]-1-(1-naphthyl)ethanamine,
(1R)-1-(1-naphthyl)-N-(1H-pyrrol-2-ylmethyl)ethanamine,
(1R)-1-(3-methoxyphenyl)-N-{[1-(phenylsulfonyl-1H-pyrrol-2-yl]methyl}ethanamine,
(1R)-1-(1-naphthyl)-N-{[1-(phenylsulfonyl)-1H-pyrrol-2-yl]methyl}ethanamine,
(1R)-1-(3-methoxyphenyl)-N-(1H-pyrrol-2-ylmethyl)ethanamine,
(1R)-1-(3-methoxyphenyl)-N-(1,3-thiazol-2-ylmethyl)ethanamine,
(1R)—N-((4-chloro-1-methyl-1H-pyrazol-3-yl)methyl)-1-(3-(methyloxy)phenyl)ethanamine,
(1R)—N-((4-chloro-1-methyl-1H-pyrazol-3-yl)methyl)-1-(1-naphthalenyl)ethanamine,
(1R)-1-(3-(methyloxy)phenyl)-N-((2-phenyl-1H-imidazol-4-yl)methyl)ethanamine,
(1R)-1-(1-naphthalenyl)-N-((2-phenyl-1H-imidazol-4-yl)methyl)ethanamine,
(1R)-1-phenyl-N-((2-phenyl-1H-imidazol-4-yl)methyl)ethanamine,
(1R)—N-((3,5-dimethyl-1-phenyl-1H-pyrazol-4-yl)methyl)-1-(3-(methyloxy)phenyl)ethanamine,
(1R)—N-((3,5-dimethyl-1-phenyl-1H-pyrazol-4-yl)methyl)-1-(4-methylphenyl)ethanamine,
(1R)—N-((3,5-dimethyl-1-phenyl-1H-pyrazol-4-yl)methyl)-1-(1-naphthalenyl)ethanamine,
(1R)—N-((3,5-dimethyl-1-phenyl-1H-pyrazol-4-yl)methyl)-1-phenylethanamine,
(1R)-1-(4-(methyloxy)phenyl)-N-((5-methyl-3-phenyl-4-isoxazolyl)methyl)ethanamine,
(1R)—N-((5-methyl-3-phenyl-4-isoxazolypmethyl)-1-(1-naphthalenyl)ethanamine,
(1R)—N-((5-methyl-3-phenyl-4-isoxazolyl)methyl)-1-phenylethanamine,
(1R)-1-(3-(methyloxy)phenyl)-N-((3-phenyl-1H-pyrazol-4-yl)methyl)ethanamine,
(1R)-1-(4-(methyloxy)phenyl)-N-((3-phenyl-1H-pyrazol-4-yl)methyl)ethanamine,
(1R)-1-(1-naphthalenyl)-N-((3-phenyl-1H-pyrazol-4-yl)methyl)ethanamine,
(1R)-1-phenyl-N-((3-phenyl-1H-pyrazol-4-yl)methyl)ethanamine,
(1R)—N-(1H-imidazol-2-ylmethyl)-1-(4-methylphenyl)ethanamine,
(1R)—N-(1H-imidazol-2-ylmethyl)-1-(1-naphthalenyl)ethanamine,
(1R)—N-((2-ethyl-4-methyl-1H-imidazol-5-yl)methyl)-1-(1-naphthalenyl)ethanamine,
(1R)—N-((2-(4-chlorophenyl)-1,3-thiazol-4-yl)methyl)-1-(4-methylphenyl)ethanamine,
(1R)—N-((2-(4-chlorophenyl)-1,3-thiazol-4-yl)methyl)-1-(1-naphthalenyl)ethanamine,
(1R)—N-((2-(4-chlorophenyl)-1,3-thiazol-4-yl)methyl)-1-(2-naphthalenyl)ethanamine,
(1R)-1-(1-naphthalenyl)-N-((2-phenyl-1,3-thiazol-4-yl)methyl)ethanamine,
(1R)—N-((3-(4-(1,1-dimethylethyl)phenyl)-1,2,4-oxadiazol-5-yl)methyl)-1-(4-methylphenyl)ethanamine,
(1R)—N-((3-(4-(1,1-dimethylethyl)phenyl)-1,2,4-oxadiazol-5-yl)methyl)-1-(2-naphthalenyl)ethanamine,
(1R)-1-(1-naphthalenyl)-N-((1-phenyl-1H-pyrazol-5-yl)methyl)ethanamine,
1-(4-fluorophenyl)-4-({[(1R)-1-(1-naphthyl)ethyl]amino}methyl)pyrrolidin-2-one,
4-({[(1R)-1-(3-chlorophenyl)ethyl]amino}methyl)-1-(4-fluorophenyl)pyrrolidin-2-one, (1R)—N-[(5-chloro-1-methyl-4-phenyl-1H-imidazol-2-yl)methyl]-1-phenylethanamine,
(1R)-1-phenyl-N-[(2-phenyl-1,3-thiazol-4-yl)methyl]ethanamine,
(1R)-1-(3-chlorophenyl)-N-{[1-(4-fluorophenyl)pyrrolidin-3-yl]methyl}ethanamine,
(1R)-1-(1-naphthyl)-N-({1-[4-(trifluoromethyl)phenyl]-1H-pyrazol-3-yl}methyl)ethanamine,
(1R)-1-(3-fluorophenyl)-N-({1-[4-(trifluoromethyl)phenyl]-1H-pyrazol-3-yl}methyl)ethanamine,
(1R)-1-(3-chlorophenyl)-N-({1-[4-(trifluoromethyl)phenyl]-1H-pyrazol-3-yl}methyl)ethanamine,
(1R)—N-({5-methoxy-1-[4-(trifluoromethyl)phenyl]-1H-pyrazol-3-yl}methyl)-1-phenylethanamine,
(1R)-1-(3-fluorophenyl)-N-({5-methoxy-1-[4-(trifluoromethyl)phenyl]-1H-pyrazol-3-yl}methyl)ethanamine,
(1R)-1-(3-chlorophenyl)-N-({5-methoxy-1-[4-(trifluoromethyl)phenyl]-1H-pyrazol-3-yl}methyl)ethanamine,
1-{5-methoxy-1-[4-(trifluoromethyl)phenyl]-1H-pyrazol-3-yl}-N-[(1R)-1-phenylethyl]ethanamine,
(1R)-1-(3-fluorophenyl)-N-(1-{5-methoxy-1-[4-(trifluoromethyl)phenyl]-1H-pyrazol-3-yl}ethyl)ethanamine,
(1R)-1-(3-chlorophenyl)-N-{1-[1-(3-chlorophenyl)-5-methoxy-1H-pyrazol-3-yl]ethyl}ethanamine,
1-[1-(3-chlorophenyl)-5-methoxy-1H-pyrazol-3-yl]-N-[(1R)-1-(3-fluorophenyl)ethyl]ethanamine,
1-(1-(3-chlorophenyl)-5-methoxy-1H-pyrazol-3-yl)-N-[(1R)-1-phenylethyl]ethanamine,
(1R)-1-(3-chlorophenyl)-N-(1-{5-methoxy-1-[4-(trifluoromethyl)phenyl]-1H-pyrazol-3-yl}ethyl)ethanamine,
1-[1-(4-bromophenyl)-5-methoxy-1H-pyrazol-3-yl]-N-[(1R)-1-(3-chlorophenyl)ethyl]ethanamine,
4-[3-(1-{[(1R)-1-(3-chlorophenyl)ethyl]amino)}ethyl)-5-methoxy-1H-pyrazol-1-yl]benzonitrile,
1-{5-methoxy-1 [6-(trifluoromethyl)pyridin-3-yl]-1H-pyrazol-3-yl}-N-[(1R)-1-phenylethyl]ethanamine,
(1R)-1-(3-fluorophenyl)-N-(1-(5-methoxy-1-[6-(trifluoromethyl)pyridin-3-yl)-1H-pyrazol-3-yl)ethyl)ethanamine,
(1R)-1-(3-chlorophenyl)-N-(1-{5-methoxy-1-6-(trifluoromethyl)pyridine-3-yl]-1H-pyrazol-3-yl)ethyl)ethanamine,
(1R)-1-phenyl-N-(1-{1 [4-(trifluoromethyl)phenyl]-1H-pyrazol-3-yl}ethyl)ethanamine,
(1R)-1-(3-fluorophenyl)-N-(1-{1-[4-(trifluoromethyl)phenyl]-1H-pyrazol-3-yl}ethyl)ethanamine,
2-methyl-N-[(1R)-1-phenylethyl-1-{1-[4-(trifluoromethyl)phenyl]-1H-pyrazol-3-yl}propan-1-amine,
(1R)-1-(3-chlorophenyl)-N-((1R)-1-(1-(4-(trifluoromethyl)phenyl)-1H-pyrazol-3-yl)ethyl)ethanamine, and
N-[(1R)-1-phenylethyl]-1-{1-[4-(trifluoromethyl)phenyl]-1H-pyrazol-3-yl}propan-1-amine.

In one aspect, the invention encompasses methods for treating a patient in need of such treatment comprising the step of administering to the patient a therapeutically effective amount of a compound of Formula I

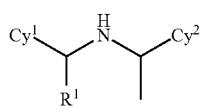

I or a pharmaceutically acceptable salt thereof, wherein:
$Cy^1$ is an unsaturated 5-membered ring comprising 1-3 heteroatoms selected from the group consisting of O, N, and S, wherein at least one of the heteroatoms is N, the ring being optionally substituted independently with 1-3 substituents selected from the group consisting of $C_{1-6}$alkyl, $C_{1-4}$haloalkyl, halogen, cyano, amino, —$OC_{1-6}$alkyl, $R^a$, and —$S(=O)_mR^a$;
m is 1 or 2;
$R^a$ is phenyl or pyridyl, either of which can be optionally substituted independently with 1-3 substituents selected from the group consisting of halogen, $C_{1-6}$alkyl, $C_{1-4}$haloalkyl, and cyano;
$R^1$ is H or $C_{1-3}$alkyl,
$Cy^2$ is phenyl or naphthyl, either of which can be optionally substituted with 1-5 substituents, wherein the substituents are selected from the group consisting from $C_{1-6}$alkyl, $C_{1-4}$haloalkyl, halogen, cyano, amino, and —$OC_{1-6}$alkyl.

In one aspect, $Cy^2$ can be optionally substituted phenyl. In one aspect, phenyl can be unsubstituted. In another aspect, phenyl can be substituted with halogen. In a further aspect, phenyl can be substituted with $C_{1-6}$alkyl or $C_{1-4}$haloalkyl.

In another aspect, $Cy^2$ can be optionally substituted naphthyl. For example, naphthyl can be unsubstituted.

In one aspect, $R^1$ can be H. In another aspect, $R^1$ can be $C_{1-3}$alkyl.

The invention provides compounds wherein $Cy^1$ is optionally substituted imidazolyl. In another aspect, $Cy^1$ can be optionally substituted pyrrolyl. In a further aspect, $Cy^1$ can be optionally substituted thiazolyl, optionally substituted pyrazolyl, optionally substituted isoxazolyl, or optionally substituted oxadiazolyl.

A. Preparation of Compounds

Methods A-E below provide exemplary synthetic methods for the preparation of the compounds of the present invention. One of skill in the art will understand that additional methods are also useful. In other words, the compounds of the invention can be made using organic synthesis using starting materials, reagents and reactions well known in the art.

Certain compounds of the invention may be conveniently prepared by a general process outlined in Scheme 1.

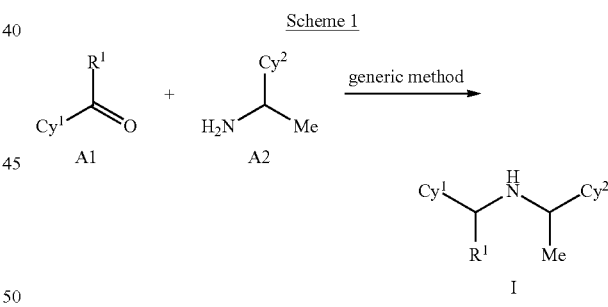

Method A: To a solution of amine A2 in dry benzene was added aldehyde ($R^1$=H) or ketone ($R^1$=alkyl) A1, anhydrous magnesium sulfate, and a catalytic amount of p-toluenesulfonic acid. The mixture was stirred and heated until imine formation was complete. The mixture was filtered through Celite®, concentrated, and dissolved in anhydrous ethanol. The ethanol solution was cooled to 0° C. and sodium borohydride was slowly added. The reaction mixture was warmed to room temperature and stirred until reaction was complete. The reaction mixture was diluted with water and extracted with EtOAc (1×). The organic phase was dried and concentrated. Purification by chromatography on silica gel or crystallization of the HCl salt from an EtOAc and hexanes solution gave amine I.

Method B: To a solution of aldehyde ($R^1$=H) or ketone ($R^1$=alkyl) Al in MeOH was added a solution of amine A2 in MeOH. The reaction mixture was shaken at room temperature until imine formation was complete. Amberlite IRA-400 supported borohydride was added and the reaction mixture was shaken at room temperature until reaction was complete. DCM and Wang-aldehyde resin (4-benzyloxybenzaldehyde, polymer-bound) were added and the reaction mixture was shaken overnight at room temperature. The resins were filtered off and washed with THF (3×0.5 mL). The solvents were evaporated under reduced pressure to give amine I.

Method C: The aldehyde ($R^1$=H) or ketone ($R^1$=alkyl) A1 was dissolved in 1,2-dichloroethane and the amine A2 was added, followed by acetic acid and finally sodium triacetoxyborohydride. The mixture was stirred overnight or until complete by TLC; upon reaction completion, the mixture was diluted with ethyl acetate, washed with saturated $NaHCO_3$ then with saturated brine, and finally dried over sodium sulphate. The solvents were evaporated under reduced pressure, to afford an oil which is purified by column chromatography on silica gel (usually Hexane/AcOEt 7/3 or DCM/MeOH 95/5). The free-base oil was then treated with 1.5-2.5 equivalents 1N HCl in diethyl ether and the solvents were evaporated under reduced pressure to afford the mono or bis-HCl salt of product I.

Method D: To a solution of aldehyde ($R^1$=H) or ketone ($R^1$=alkyl) A1 and amine A2 in THF was added titanium isopropoxide or titanium tetrachloride. The reaction was stirred until imine formation was complete, cooled to –78° C., and a solution of $NaBH_4$ in MeOH was added. After stirring at –78° C. for 1 h, the reaction mixture was quenched with concentrated $NH_4OH$ and filtered. The filtrate was concentrated and purified via column chromatography on silica gel (EtOAc in hexanes) to give amine I.

Certain compounds of the invention may be conveniently prepared by a general process outlined in Scheme 2.

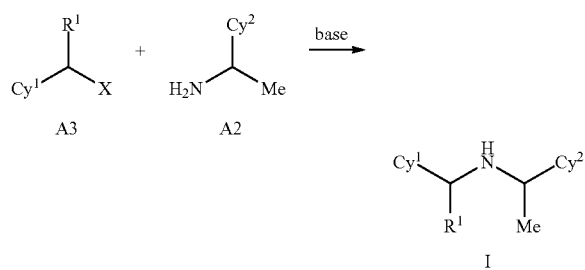

Scheme 2

Method E: To chloride (X=Cl) A3 was added a solution of amine A2 in 1:1 THF/$H_2O$. Ambersep 900 supported carbonate or other base was added and the reaction mixture was shaken at 55° C. DCM was added followed by Wang-aldehyde resin (4-benzyloxybenzaldehyde, polymer-bound) and the mixture was shaken for 5 h at 55° C. and room temperature for 2 d. The resins were filtered off and washed with MeOH (3×0.5 mL). The solvents were evaporated under reduced pressure to give amine I.

Regarding the molecular structures set forth in Methods A-E above, one of skill in the art will readily appreciate that precursors and intermediates having aryl groups other than $Cy^2$=phenyl, e.g. naphthyl, can be used to practice the synthetic methods.

B. Pharmaceutical Compositions and Administration

Compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecyl sulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J. Pharm. Sci.* 66: 1, 1977. In certain embodiments of the invention salts of hydrochloride and salts of methanesulfonic acid can be used.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the calcium receptor-active compound in the compositions useful in the invention can range from about 0.1 mg to about 180 mg, for example from about 5 mg to about 180 mg, or from about 1 mg to about 100 mg of the calcimimetic compound per subject. In some aspects, the therapeutically effective amount of calcium receptor-active compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a calcium receptor-active compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcium receptor-active compound when provided as a single dose, in multiple doses, or as a partial dose. Thus, an effective dosage amount of the calcium receptor-active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the calcimimetic compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

III. Therapeutic Uses of the Compounds of the Invention

Compounds and compositions of the present application which act on calcium receptors may thus be used, in one aspect, for the treatment or prevention of diseases or disorders linked with abnormal physiological behaviour of calcium receptors such as membrane calcium receptors capable of binding extracellular calcium.

A patient in need of the treatment, as used herein, is a human having a disease or disorder characterized by one or more of the following: (1) abnormal calcium ion homeostasis, (b) an abnormal level of a messenger whose production or secretion is affected by the calcium sensing receptor (CaSR) activity, or (3) an abnormal level of activity of a messenger whose function is affected by the calcium sensing receptor activity. In one aspect, the patient has a disease or disorder characterized by an abnormal level of one or more calcium sensing receptor-regulated components and the compound is active on a CaSR of a cell including parathyroid cell, bone osteoclast, juxtaglomerular kidney cell, Kidney messengial cell, glomerular kidney cell, proximal tubule kidney cell, distal tubule kidney cell, cell of the thick ascending limb of Henle's loop and/or collecting duct, parafolliculr cell in the thyroid (C-cell), intestinal cell, platelet, vascular smooth muscle cell, GI tract cell, pituitary cell, or hypothalamic cell.

Diseases characterized by abnormal calcium homeostasis include hyperparathyroidism and the like (as described, e.g., in standard medical textbooks, such as "Harrison's Principles of Internal Medicine". The compounds and compositions of the present invention can be used, in particular, to participate in a reduction of the serum levels in the parathyroid hormone known as PTH: these products could thus be useful, in one aspect, for the treatment of diseases such as hyperparathyroidism. Similarly, abnormalities in calcium homeostasis, such as hypercalcaemia, can be treated with these compounds. Further, the compounds of the invention can treat hyperplasia and parathyroid adenoma. In another aspect, the compounds of the invention can have properties which enable them to reduce bone resorption which depends directly on the fluctuation of circulating PTH levels: these products could be useful, in particular, for the treatment of diseases such as osteoporosis, osteopaenia Paget's disease and the reconstruction of fractures. They can also be used in the treatment and prophylaxis of polyarthritis and osteoarthritis.

In one aspect, the invention provides a method of inhibiting, decreasing or preventing vascular calcification in an individual. The method comprises administering to the individual a therapeutically effective amount of the calcimimetic compound of the invention. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits.

In one aspect, the compounds of the invention may be used to prevent or treat atherosclerotic calcification and medial calcification and other conditions characterized by vascular calcification. In one aspect, vascular calcification may be associated with chronic renal insufficiency or end-stage renal disease. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

In one aspect, administration of an effective amount of the compounds of the invention can reduce serum PTH without causing aortic calcification. In another aspect, administration of the compounds of the invention can reduce serum creatinine level or can prevent increase of serum creatinine level. In another aspect, administration of the compounds of the invention can attenuates parathyroid (PT) hyperplasia.

The compounds of the invention may be administered alone or in combination with other drugs for treating vascular calcification, such as vitamin D sterols and/or RENAGEL®. Vitamin D sterols can include calcitriol, alfacalcidol, doxercalciferol, maxacalcitol or paricalcitol. In one aspect, the compounds of the invention can be administered before or after administration of vitamin D sterols. In another aspect, the compounds of the invention can be co-administered with vitamin D sterols. The methods of the invention can be practiced to attenuate the mineralizing effect of calcitriol on vascular tissue. In one aspect, the methods of the invention can be used to reverse the effect of calcitriol of increasing the serum levels of calcium, phosphorus and CaxP product thereby preventing or inhibiting vascular calcification. In another aspect, the compounds of the invention can be used to stabilize or decrease serum creatinine levels. In one aspect, in addition to creatinine level increase due to a disease, a further increase in creatinine level can be due to treatment with vitamin D sterols such as calcitriol. In addition, the compounds of the invention may be administered in conjunction with surgical and non-surgical treatments. In one aspect, the methods of the invention can be practiced in injunction with dialysis.

In one aspect, the compounds of the invention can be used for treating abnormal intestinal motilities disorders such as diarrhea. The methods of the invention comprise administering to the individual a therapeutically effective amount of the compounds of Formula I.

As used herein, the term "diarrhea" refers to a condition of three or more unformed stools in a 24-hour period of volume more than 200 g per day. In one aspect, diarrhea can be osmotic, i.e., resulting if the osmotic pressure of intestinal contents is higher than that of the serum. This condition may result from malabsorption of fat (e.g., in celiac disease) or of lactose (e.g., in intestinal lactase deficiency), or it can happen due to the use of certain laxatives (e.g., lactulose, magnesium hydroxide) or artificial sweeteners (e.g., sorbitol, mannitol). In another aspect, diarrhea can be secretory, i.e., occurring when there is a net secretion of water into the lumen. This may occur with bacterial toxins (such as those produced, e.g., by *E. coli* and *Vibrio cholerae*), or with hormones, such as vasoactive intestinal polypeptide, which is produced by rare islet cell tumors (pancreatic cholera). Both osmotic and secretory diarrheas result from abnormalities in the small intestine such that the flow of water through the ileocecal area overcomes the absorptive capacity of the colon.

In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with chemotherapy, radiation treatment, inflammation or toxic traumatic injury. In another aspect, exudative diarrhea can be associated with a gastrointestinal or abdominal surgery.

In another aspect, diarrhea can be due to acceleration of intestinal transit (rapid transit diarrhea). Such condition may occur because the rapid flow-through impairs the ability of the gut to absorb water.

In one aspect, the invention provides the compounds and compositions for treating abnormal gastric fluid secretion/absorption disorders in conjunction with treating underlying causes of for example, diarrhea or with other treatment methods. In one aspect, calcimimetics can be administered to a subject before, after or concurrently with oral rehydration therapy. For example, oral rehydration therapy may contain the following ingredients: sodium, potassium, chloride, bicarbonate, citrate and glucose. In another aspect, the compounds of the invention can be administered to a subject before, after or concurrently with an antimotility agent, such as loperamide (Imodium), diphenoxylate, or bismuth subsalicylate (Pepto-Bismol). In another aspect, calcimimetics can be administered with antibiotics (e.g., trimethoprim-sulfamethoxazole (Bactrim DS), ciprofloxacin (Cipro), norfloxacin (Noroxin), ofloxacin (Floxin), doxycycline (Vibramycin), erythromycin). In one aspect, the compounds of the invention can be administered together with calcium or polyamines such as spermine, spermidine, putrescine, and ornithine metabolites or amino acids such of L-tryptophan, L-phenylalanine. In another aspect, the compounds of the invention can be administered together with sodium and glucose. In addition, the compounds of the invention may be administered in conjunction with surgical and non-surgical treatments.

The invention further provides methods for modulating intestinal fluid secretion and absorption. In one aspect, the purpose can be to increase fluid absorption and/or decrease fluid secretion in a subject and thus the methods of the invention can comprise administering an effective amount of a pharmaceutical composition comprising a compound of the invention.

The invention provides methods of modulation the absorption or secretion of a drug, poison or nutrient in the intestinal tract of a subject, comprising administering an effective amount of a pharmaceutical composition comprising a compound of the invention together with a pharmaceutically acceptable carrier to the subject. In one aspect, the invention provides methods of treatment of a malassimilation or a malabsorption of a subject, comprising administering an effective amount of a pharmaceutical composition comprising a compound of Formula I together with a pharmaceutically acceptable carrier to the subject.

As used herein, the term "malassimilation" encompasses impaired processes of food digestions and absorption occurring in one of two ways (1) through intraluminal disorders (maldigestion of food) and (2) through intramural disorders (malabsorption of food).

Methods of the invention comprising administering a pharmaceutical composition of the invention can also be practiced to treat malnutrition in a subject. For example, a subject can be malnourished if the subject is grossly underweight (weight for height is below 80% of the standard), grossly overweight (weight for height above 120% of the standard), if the subject unintentionally lost 10% or more of body weight, has a gastrointestinal tract surgery, experienced nutrient losses (e.g., from diarrhea, dialysis, vomiting), has increased metabolic needs (e.g., due to pregnancy, lactation, increased physical activity, fever, injury), is an alcoholic or chronic drug user (antibiotics, antidepressants, diuretics), has medical conditions which interfere with nutrient intake, absorption, metabolism, or utilization, has poor dentition (particularly in the elderly subjects), or has mouth sores due to herpes, HIV or chemotherapy. In another aspect, the subject can be malnourished due to dietary risk factors (e.g., loss of appetite, inadequate food or nutrient intake, lack of variety of foods, fad, weight-loss diets, inadequate fiber, excessive fat, sodium, sugar, excess alcohol, eats too few fruits, vegetables) or due to social risk factors (e.g., chronic ill health, poverty, inadequate money to buy food, low socioeconomic status, immobility or inability to purchase, store, or cook food, social isolation, eats alone most of the time, substance abuser, conditions which limit subject's ability to eat). Further, the methods of the invention can be practiced when a subject has limited access to nutrients such as during survival following environmental disasters, survival at sea, marooning and deep-sea living or space travel.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intraglomerular pressure; (v) synthesis and maintenance of the glomerular basement membrane (GMB); (iv) production and secretion of vascular endothelial growth factor (VEGF) required for the glomerular endothelial cell (GEN) integrity.

Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgestic or anticancer agent), an organ failure, an organ transplantation, or uropathy. In one aspect, ischemia can be sickle-cell anemia, thrombosis, transplantation, obstruction, shock or blood loss. In on aspect, the genetic disorders may include congenital nephritic syndrome of the Finnish type, the fetal membranous nephropathy or mutations in podocyte-specific proteins, such as α-actin-4, podocin and TRPC6.

In one aspect, the podocyte-related disease or disorder can be an abnormal expression or function of slit diaphragm proteins such as podocin, nephrin, CD2AP, cell membrane proteins such as TRPC6, and proteins involved in organization of the cytoskeleton such as synaptopodin, actin binding proteins, lamb-families and collagens. In another aspect, the podocyte-related disease or disorder can be related to a disturbance of the GBM, to a disturbance of the mesangial cell function, and to deposition of antigen-antibody complexes and anti-podocyte antibodies.

In one aspect, the podocyte-related disease or disorder can be proteinuria, such as microalbumiuria or macroalbumiuria. In another aspect, the podocyte-related disease or disorder can be tubular atrophy.

In one aspect, the present invention provides method of treatment or prevention of inflammatory bowel disease using the compounds of the invention. Inflammatory bowel disease, or IBD, as used herein, is a disease characterized by inflammation or ulcerations in the small and/or large intestine with chronically recurring symptoms of abdominal pain and alteration in bowel habits. IBD has been classified into the broad categories of Crohn's disease (CD) and ulcerative colitis (UC). In one aspect, the invention provides methods for treating UC using calcimimetic compounds and compositions. In another aspect, the methods of the invention can be used for treatment of CD using calcimimetic compounds and compositions. In one aspect, methods of the present invention result in prevention of onset or alleviation of one or more signs or symptoms of UC or CD. Table 1 further summarizes inflammatory markers in pathophysiology of IBD and signs/symptoms commonly found in ulcerative colitis and Crohn's disease.

TABLE 1

| Sign/Symptom | Ulcerative Colitis | Crohn's Disease |
| --- | --- | --- |
| Area of intestinal tract affected | Any part of innermost lining of colon, continuous with no patches of normal tissues | Lower ileum most common but can flare up anywhere, including the colon, patches of normal tissue between affected areas; can affect entire intestinal wall |
| Diarrhea | Typically four episodes per day | Typically four episodes per day |
| Abdominal pain/cramping | Mild tenderness, lower abdominal cramping | Moderate to severe abdominal tenderness in right lower quadrant |
| Blood in stool | Present; amount depends on disease severity | May be present; amount depends on disease severity |
| Fatigue | Result of excessive blood loss and anemia | Result of excessive blood loss, anemia, and poor nutrient absorption |
| Fever | Low-grade in severe cases | Low-grade in severe cases |
| Physical examination | Rectal exam may show perianal irritation, fissures, hemorrhoids, fistulas, and abscesses | Peritoneal irritation, abdominal or pelvis mass |
| Weight loss/anorexia | Weight loss in more severe cases | Weight loss and anorexia common due to poor digestion and intestinal absorption |
| Appetite | Often decreased during periods of disease exacerbation | Often decreased during periods of disease exacerbation |
| Risk of colon cancer | Increased | Increased |

In one aspect, the present invention provides method of treatment or prevention of irritable bowel syndrome. Irritable bowel syndrome, or IBS, as used herein, is a gastrointestinal disorder characterized by altered bowel habits and abdominal pain, typically in the absence of detectable structural abnormalities or biochemical cause. The Rome II criteria can be used to diagnose IBS and rule out other disorders. The criteria include at least 3 months of the following continuous recurrent symptoms: abdominal pain or discomfort that is relieved by defecation or is associated with a change in the frequency or consistency of stool, and disturbed defecation involving two or more of the following characteristics at least 25% of the time: altered stool frequency, altered stool form (e.g., lumpy or hard, or loose or watery), altered stool passage (e.g., straining, urgency, or feeling of incomplete evacuation), passage of mucus, bloating or feeling of abdominal distention. The intensity and location of abdominal pain in IBS can be highly variable, even within an individual patient: it is localized to the hypogastrium in 25%, the right side in 20%, the left side in 20%, and the epigastrium in 10% of the patients. The pain can be generally crampy or achy, although sharp, dull, gas-like, or non-descript pains are also common. In one aspect, patients with IBS may present with constipation (IBS-C, constipation predominant IBS), diarrhea (IBS-D, diarrhea-predominant IBS), or constipation alternating with diarrhea (IBS-A, mixed symptom IBS, or "alternators"). Long period of straining may be required for fecal evaluation both in constipation- and diarrhea-predominant patient. Constipation may persist for weeks to months, interrupted by brief periods of diarrhea. Feelings of incomplete fecal evacuation may lead to multiple attempts at stool passage daily. In patients with IBS-D, stools are characteristically loose and frequent but of normal daily volume. Mucus discharge has been reported in up to 50% of patients with IBS. Upper gut symptoms are common in IBS, with 25% to 50% of patients reporting heartburn, early satiety, nausea, and vomiting, up to 87% note intermittent dyspepsia. Agreus L. et al. (1995) Gastroenterology 109: 671. Extraintestinal complaints in patients with IBS include chronic pelvic pain, fibromyalgia, genitourinary dysfunctions, such as dysmenorrheal, dyspareunia, impotence, urinary frequency, nocturia, and a sensation of incomplete bladder emptying. Impaired sexual function is reported by 83% of patients with IBS. Patients with functional bowel disorders have higher incidences of hypertension, headaches, peptic ulcer disease, rashes than the general population and more commonly report fatigue, loss of concentration, insomnia, palpitations, and unpleasant tastes in the mouth.

While the pathogenesis of IBS is poorly understood, it has been proposed that abnormal gut motor and sensory activity, central neural dysfunction, psychological disturbances, stress and luminal factors play a role. IBS has been associated with colonic and small intestinal motility abnormalities, as well as with motor abnormalities in other smooth muscle sites. The visceral sensory abnormalities, which may be responsible for sensations of pain, gas, or bloating in IBS, have been a major focus of investigation. Perception of abdominal symptoms is mediated by afferent neural pathways which are activated by visceral stimuli acting on chemoreceptors, mechanoreceptors, and receptors in the mesentery which may play a role in painful stimulation of the gut. Information from these activated receptors is carried in spinal afferent nerves and thus transmitted to the brain where conscious perception occurs. It is postulated that IBS results from sensitization of afferent pathways such that normal physiological gut stimuli not perceived by healthy individuals induce pain in the patient with IBS. The sensitizing event responsible for induction of symptoms in IBS is unknown. The clinical association of emotional disorders and stress with symptom exacerbation and the therapeutic response to therapies that act on cerebral cortical sites strongly suggests the role of central nervous system factors in the pathogenesis of IBS. However, it is unclear whether IBS represents a primary gut disturbance with inappropriate input from the central nervous system or a central nervous system disorder with centrally directed changes in gut motor and sensory activity. Further, both mental stress and administration of the cholinesterase inhibitor neostigmine evoke increases in colonic motility and changes in electroencephalographic waveforms which are exaggerated in patients with IBS compared to healthy volunteers, suggesting that both the gut and brain are hypersensitive in IBS. Investigations of the effects of stress reinforce the importance of the brain-gut axis in the regulation of colonic activities. A strongly positive relationship has been reported between daily stress and daily symptoms in women with IBS. Levy R. et al. (1997) J. Behav. Med. 20: 177.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in Examples. Various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence. The structure of the prepared compounds is verified by mass spectral data. For some compounds, ions having mass greater than M+H are reported. These ions generally represent dimers or trimers of the synthesized compound, and in some instances represent trifluoroacetate adducts generated from the mobile phase of the LC/MS. The trifluoroacetate adducts will have a weight of M+115.

Example 1

The compounds shown in Table 2 below were prepared by the following general procedure.

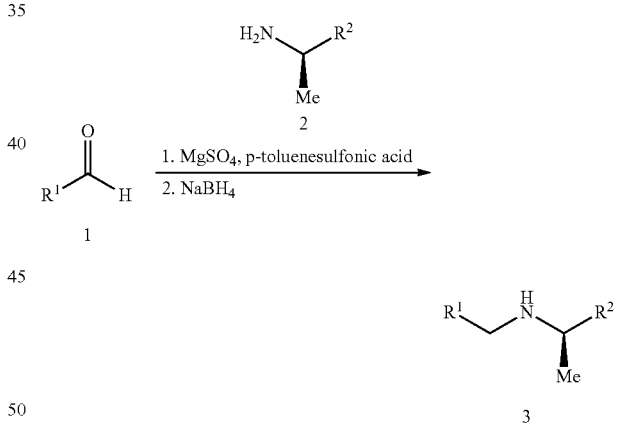

To a solution of amine 2 (1.98 mmol) in dry benzene (15 mL) was added aldehyde 1 (1.98 mmol), anhydrous magnesium sulfate (~0.5 g), and a catalytic amount of p-toluenesulfonic acid. The mixture was stirred and heated to 80° C. for 12-24 h. The mixture was filtered through Celite®, concentrated, and dissolved in anhydrous ethanol. The ethanol solution was cooled to 0° C. and sodium borohydride (4.1 mmol) was slowly added. The reaction mixture was warmed to room temperature and stirred for 12-15 h. The reaction mixture was diluted with water and extracted with EtOAc (1×). The organic phase was dried and concentrated. Purification by chromatography on silica gel or crystallization of the HCl salt from an EtOAc and hexanes solution gave amine 3.

TABLE 2

| Comp | Structure | Name | m/z |
|---|---|---|---|
| 4 | 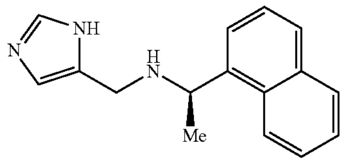 | (1R)-N-(1H-imidazol-5-ylmethyl)-1-(1-naphthyl)ethanamine | 252.1 |
| 5 | 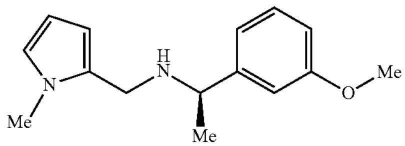 | (1R)-1-(3-methoxyphenyl)-N-[(1-methyl-1H-pyrrol-2-yl)methyl]ethanamine | 245.1 |
| 6 | 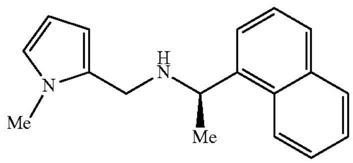 | (1R)-N-[(1-methyl-1H-pyrrol-2-yl)methyl]-1-(1-naphthyl)ethanamine | 265.1 |
| 7 | 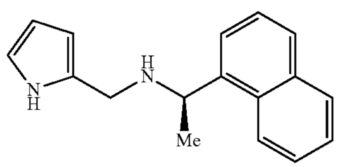 | (1R)-1-(1-naphthyl)-N-(1H-pyrrol-2-ylmethyl)ethanamine | 251.1 |
| 8 | 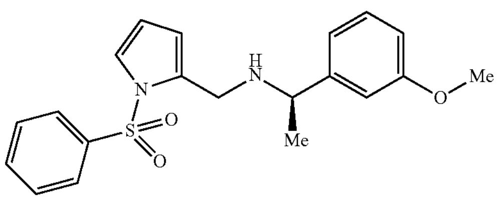 | (1R)-1-(3-methoxyphenyl)-N-{[1-(phenylsulfonyl)-1H-pyrrol-2-yl]methyl}ethanamine | 371.1 |
| 9 | 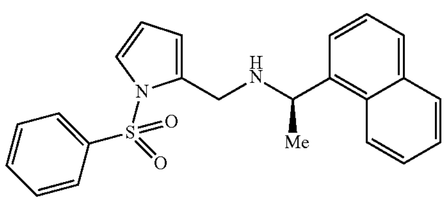 | (1R)-1-(1-naphthyl)-N-{[1-(phenylsulfonyl)-1H-pyrrol-2-yl]methyl}ethanamine | 391.1 |
| 10 | 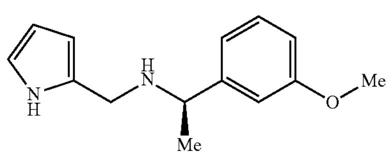 | (1R)-1-(3-methoxyphenyl)-N-(1H-pyrrol-2-ylmethyl)ethanamine | 231.1 |
| 11 | 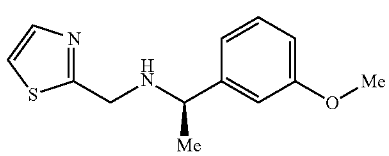 | (1R)-1-(3-methoxyphenyl)-N-(1,3-thiazol-2-ylmethyl)ethanamine | 249.1 |

Example 2

The compounds shown in Table 3 below were prepared by the following general procedure.

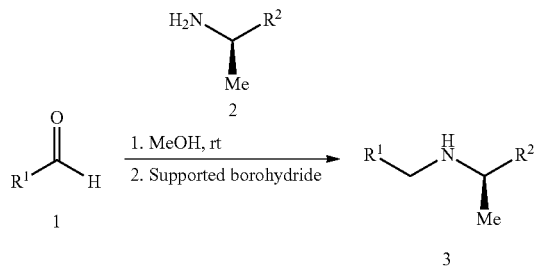

To a solution of aldehyde 1 (0.5 mmol) in MeOH (0.75 mL) was added a solution of amine 2 (0.6 mmol) in MeOH (0.75 mL). The reaction mixture was shaken at room temperature overnight. Amberlite IRA-400 supported borohydride (1 mmol) was added and the reaction mixture was shaken overnight at room temperature. DCM (1 mL) and Wang-aldehyde resin (4-benzyloxybenzaldehyde, polymer-bound; 0.2 mmol) were added and the reaction mixture was shaken overnight at room temperature. The resins were filtered off and washed with THF (3×0.5 mL). The solvents were evaporated under reduced pressure to give amine 3.

TABLE 3

| Comp | Structure | Name | m/z |
|---|---|---|---|
| 12 | 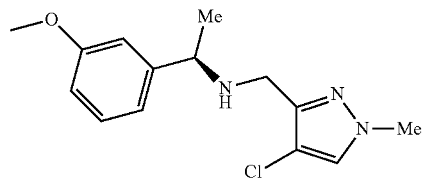 | (1R)-N-((4-chloro-1-methyl-1H-pyrazol-3-yl)methyl)-1-(3-(methyloxy)phenyl)ethanamine | 280.1 |
| 13 | 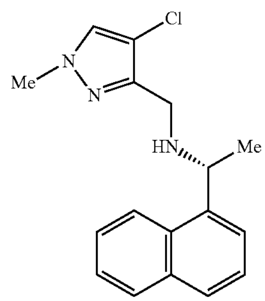 | (1R)-N-((4-chloro-1-methyl-1H-pyrazol-3-yl)methyl)-1-(1-naphthalenyl)ethanamine | 300.1 |
| 14 | 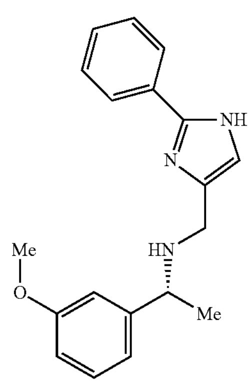 | (1R)-1-(3-(methyloxy)phenyl)-N-((2-phenyl-1H-imidazol-4-yl)methyl)ethanamine | 308.2 |
| 15 | 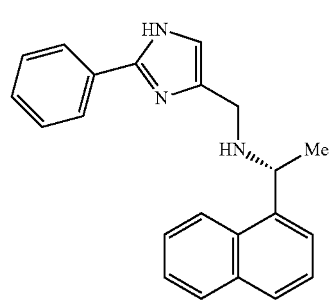 | (1R)-1-(1-naphthalenyl)-N-((2-phenyl-1H-imidazol-4-yl)methyl)ethanamine | 328.2 |

TABLE 3-continued

| Comp | Structure | Name | m/z |
|---|---|---|---|
| 16 | 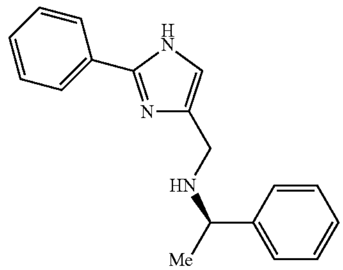 | (1R)-1-phenyl-N-((2-phenyl-1H-imidazol-4-yl)methyl)ethanamine | 278.2 |
| 17 | 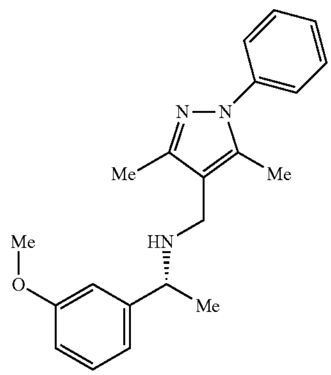 | (1R)-N-((3,5-dimethyl-1-phenyl-1H-pyrazol-4-yl)methyl)-1-(3-(methyloxy)phenyl)ethanamine | 336.2 |
| 18 | 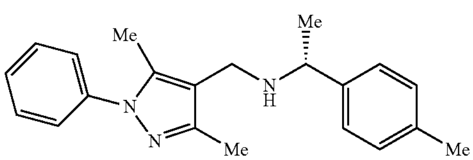 | (1R)-N-((3,5-dimethyl-1-phenyl-1H-pyrazol-4-yl)methyl)-1-(4-methylphenyl)ethanamine | 320.2 |
| 19 | 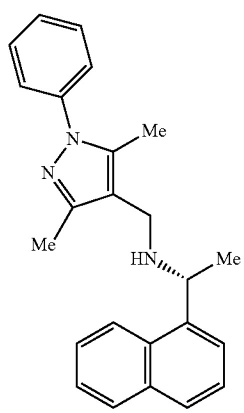 | (1R)-N-((3,5-dimethyl-1-phenyl-1H-pyrazol-4-yl)methyl)-1-(1-naphthalenyl)ethanamine | 356.2 |
| 20 | 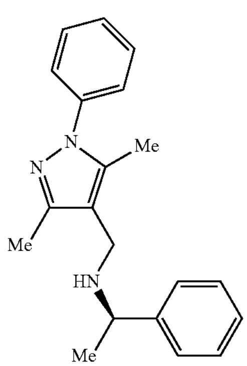 | (1R)-N-((3,5-dimethyl-1-phenyl-1H-pyrazol-4-yl)methyl)-1-phenylethanamine | 306.2 |

TABLE 3-continued

| Comp | Structure | Name | m/z |
|---|---|---|---|
| 21 | 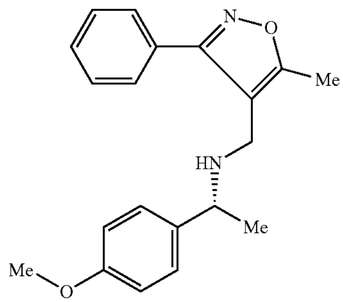 | (1R)-1-(4-(methyloxy)phenyl)-N-((5-methyl-3-phenyl-4-isoxazolyl)methyl)ethanamine | 323.2 |
| 22 | 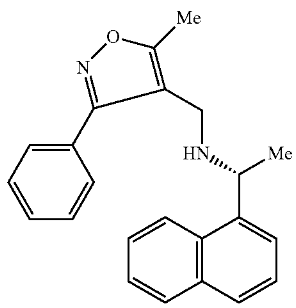 | (1R)-N-((5-methyl-3-phenyl-4-isoxazolyl)methyl)-1-(1-naphthalenyl)ethanamine | 343.2 |
| 23 | 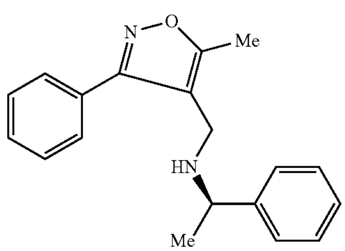 | (1R)-N-((5-methyl-3-phenyl-4-isoxazolyl)methyl)-1-phenylethanamine | 293.1 |
| 24 | 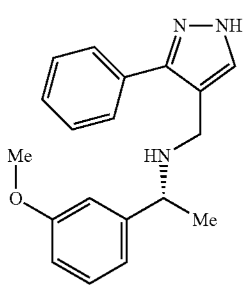 | (1R)-1-(3-(methyloxy)phenyl)-N-((3-phenyl-1H-pyrazol-4-yl)methyl)ethanamine | 308.2 |
| 25 | 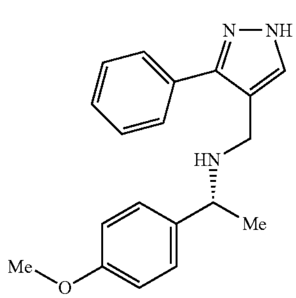 | (1R)-1-(4-(methyloxy)phenyl)-N-((3-phenyl-1H-pyrazol-4-yl)methyl)ethanamine | 308.2 |

TABLE 3-continued

| Comp | Structure | Name | m/z |
|---|---|---|---|
| 26 | 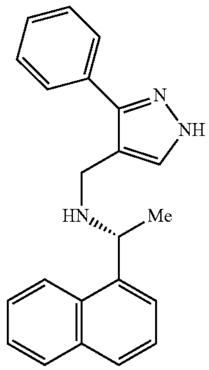 | (1R)-1-(1-naphthalenyl)-N-((3-phenyl-1H-pyrazol-4-yl)methyl)ethanamine | 328.2 |
| 27 | 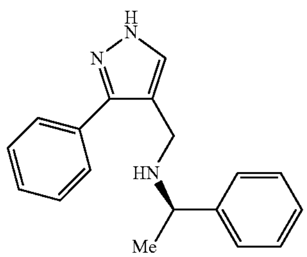 | (1R)-1-phenyl-N-((3-phenyl-1H-pyrazol-4-yl)methyl)ethanamine | 278.2 |
| 28 | 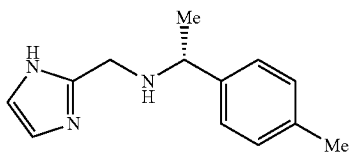 | (1R)-N-(1H-imidazol-2-ylmethyl)-1-(4-methylphenyl)ethanamine | 216.2 |
| 29 | 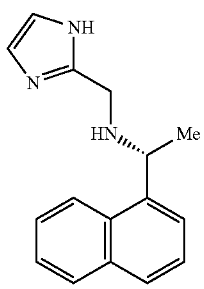 | (1R)-N-(1H-imidazol-2-ylmethyl)-1-(1-naphthalenyl)ethanamine | 252.2 |
| 30 | 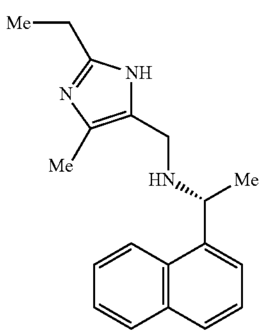 | (1R)-N-((2-ethyl-4-methyl-1H-imidazol-5-yl)methyl)-1-(1-naphthalenyl)ethanamine | 294.2 |

Example 3

The compounds shown in Table 4 below were prepared by the following general procedure.

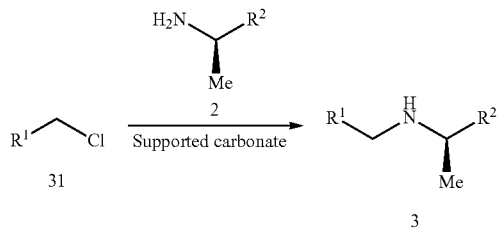

To chloride 31 (0.5 mmol) was added a solution of amine 2 (0.6-0.75 mmol) in 1:1 THF/H$_2$O (1.5 mL). Ambersep 900 supported carbonate (1 mmol) was added and the reaction mixture was shaken overnight at 55° C. DCM (2 mL) was added followed by Wang-aldehyde resin (4-benzyloxybenzaldehyde, polymer-bound) and the mixture was shaken for 5 h at 55° C. and room temperature for 2 d. The resins were filtered off and washed with MeOH (3×0.5 mL). The solvents were evaporated under reduced pressure to give amine 3.

TABLE 4

| Comp | Structure | Name | m/z |
|---|---|---|---|
| 32 | 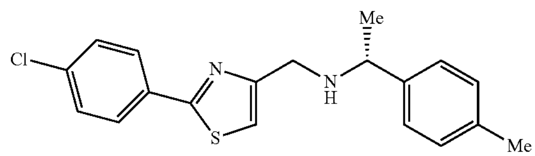 | (1R)-N-((2-(4-chlorophenyl)-1,3-thiazol-4-yl)methyl)-1-(4-methylphenyl)ethanamine | 343.1 |
| 33 | 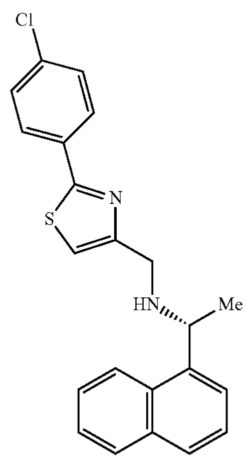 | (1R)-N-((2-(4-chlorophenyl)-1,3-thiazol-4-yl)methyl)-1-(1-naphthalenyl)ethanamine | 379 |
| 34 | 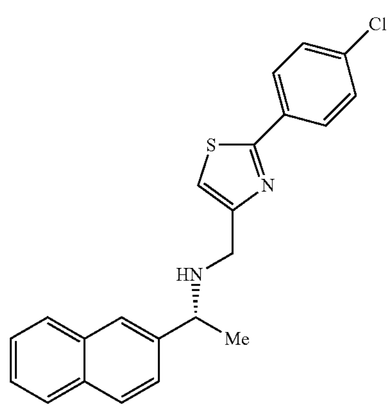 | (1R)-N-((2-(4-chlorophenyl)-1,3-thiazol-4-yl)methyl)-1-(2-naphthalenyl)ethanamine | 379.1 |

TABLE 4-continued

| Comp | Structure | Name | m/z |
|---|---|---|---|
| 35 | 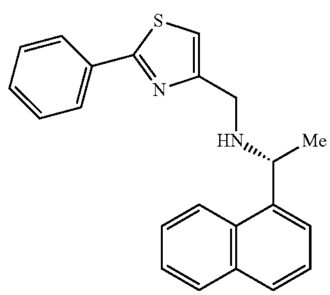 | (1R)-1-(1-naphthalenyl)-N-((2-phenyl-1,3-thiazol-4-yl)methyl)ethanamine | 345.1 |
| 36 | 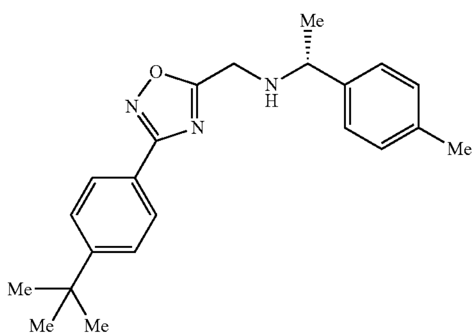 | (1R)-N-((3-(4-(1,1-dimethylethyl)phenyl)-1,2,4-oxadiazol-5-yl)methyl)-1-(4-methylphenyl)ethanamine | 350.2 |
| 37 | 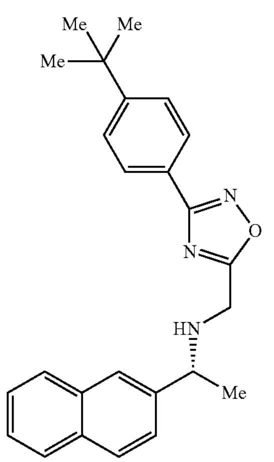 | (1R)-N-((3-(4-(1,1-dimethylethyl)phenyl)-1,2,4-oxadiazol-5-yl)methyl)-1-(2-naphthalenyl)ethanamine | 386.2 |

Example 4

Synthesis of (1R)-1-(1-naphthalenyl)-N-((1-phenyl-1H-pyrazol-5-yl)methyl)ethanamine

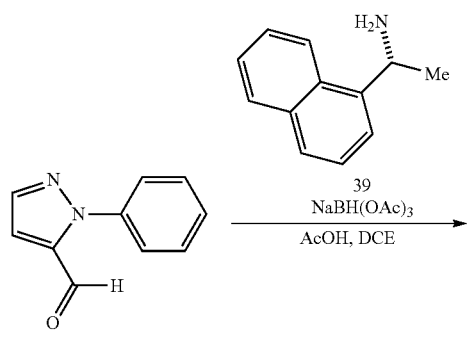

To a solution of 1-phenyl-1H-pyrazole-5-carbaldehyde 38 (0.517 g, 3 mmol) in DCE (10 mL) at room temperature was added (R)-1-(naphthalen-1-yl)ethanamine 39 (0.625 g, 4 mmol), acetic acid (0.208 g, 3 mmol), and NaBH(OAc)$_3$ (0.946 g, 4 mmol). The reaction mixture was stirred at room temperature for 18 h, quenched with saturated NaHCO$_3$, diluted with EtOAc, washed with saturated NaHCO$_3$ (1×), brine (1×), dried over MgSO$_4$, filtered, and concentrated. Purification by flash column chromatography on silica gel (eluted with 20% to 70% EtOAc in hexanes) gave (1R)-1-(1-naphthalenyl)-N-((1-phenyl-1H-pyrazol-5-yl)methyl)ethanamine 40. Mass spectrum: calculated for $C_{22}H_{21}N_3$ 327.2; found 328.2 (M$^+$+1).

Example 5

Synthesis of (1R)—N-[(5-chloro-1-methyl-4-phenyl-1H-imidazol-2-yl)methyl]-1-phenylethanamine

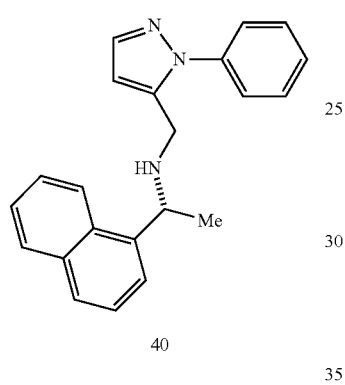

Step 1. To a solution of 4-phenyl-1H-imidazole 41 (2.01 g, 13.9 mmol) in DMF (30 mL) containing cesium carbonate (6.05 g, 18.6 mmol) at room temperature was added iodomethane (0.950 mL, 15.3 mmol). The reaction mixture was stirred at room temperature for 5 h, diluted with EtOAc, washed with water (1×), brine (1×), dried over MgSO$_4$, filtered, and concentrated. Purification by flash column chromatography on silica gel (70% to 100% EtOAc in hexanes) gave 1-methyl-4-phenyl-1H-imidazole 42. Mass spectrum: calculated for $C_{10}H_{10}N$ 158.1; found 159.2 (M$^+$+1).

Step 2. To a solution of 1-methyl-4-phenyl-1H-imidazole 42 (0.512 g, 3.24 mmol) in THF (15 mL) at −40° C. was added n-butyllithium (2.40 mL, 3.84 mmol) (1.6 M in hexanes), stirred at −40° C. for 30 min, cooled to −78° C., and N,N- dimethylformamide (0.325 mL, 4.21 mmol) was added. The reaction mixture was warmed to room temperature over 1 h, stirred at room temperature for 2 h, diluted with EtOAc, washed with water (1×), brine (1×), dried over MgSO$_4$, filtered, and concentrated. The crude product was dissolved in DCM (~20 mL), diluted with hexanes (~50 mL), and concentrated to a volume of approximately 30 mL. The solution was cooled to 0° C. and the solid was collected by filtration, washed with hexanes, and dried under high vacuum to give 1-methyl-4-phenyl-1H-imidazole-2-carbaldehyde 43. Mass spectrum: calculated for $C_{11}H_{10}N_2O$ 186.1; found 187.1 ($M^+$+1).

Step 3. To a solution of 1-methyl-4-phenyl-1H-imidazole-2-carbaldehyde 43 (0.299 g, 1.61 mmol) in CCl$_4$ (6 mL) was added N-chlorosuccinimide (229 mg, 1.72 mmol). The reaction mixture was heated to reflux for 4 h, cooled to room temperature, filtered, and concentrated. Purification by flash column chromatography on silica gel (5% to 20% EtOAc in hexanes) gave 5-chloro-1-methyl-4-phenyl-1H-imidazole-2-carbaldehyde 44. Mass spectrum: calculated for $C_1H_9ClN_2O$ 220.0; found 221.3 ($M^+$+1).

Step 4. (1R)—N-[(5-Chloro-1-methyl-4-phenyl-1H-imidazol-2-yl)methyl]-1-phenylethanamine 46 was prepared using the same procedure given in Example 4 substituting (R)-1-(naphthalen-1-yl)ethanamine 39 for (R)-1-phenylethanamine 45. Mass spectrum: calculated for $C_{19}H_{20}ClN_3$ 325.1; found 326.2 ($M^+$+1).

Example 6

Synthesis of (1R)-1-phenyl-N-[(2-phenyl-1,3-thiazol-4-yl)methyl]ethanamine

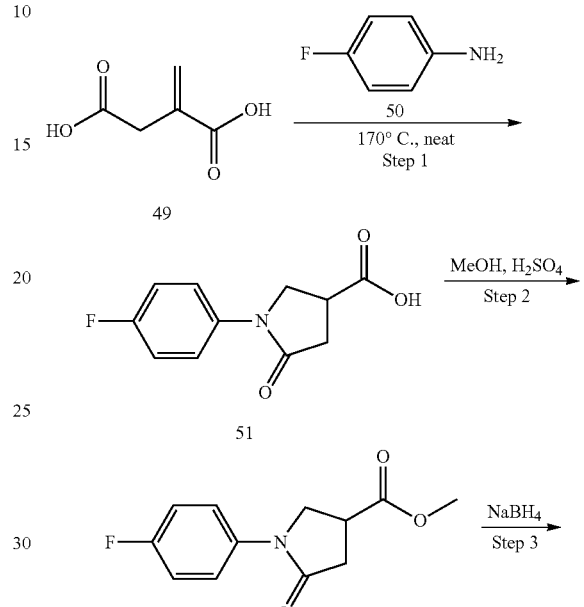

(1R)-1-phenyl-N-[(2-phenyl-1,3-thiazol-4-yl)methyl]ethanamine 48 was prepared using the same procedure given in Example 4 except substituting (R)-1-(naphthalen-1-yl)ethanamine 39 for (R)-1-phenylethanamine 45. Mass spectrum: calculated for $C_{18}H_{18}N_2S$ 294.1; found 295.2 ($M^+$+1).

Example 7

Synthesis of 4-({[(1R)-1-(3-chlorophenyl)ethyl]amino}methyl)-1-(4-fluorophenyl)pyrrolidin-2-one

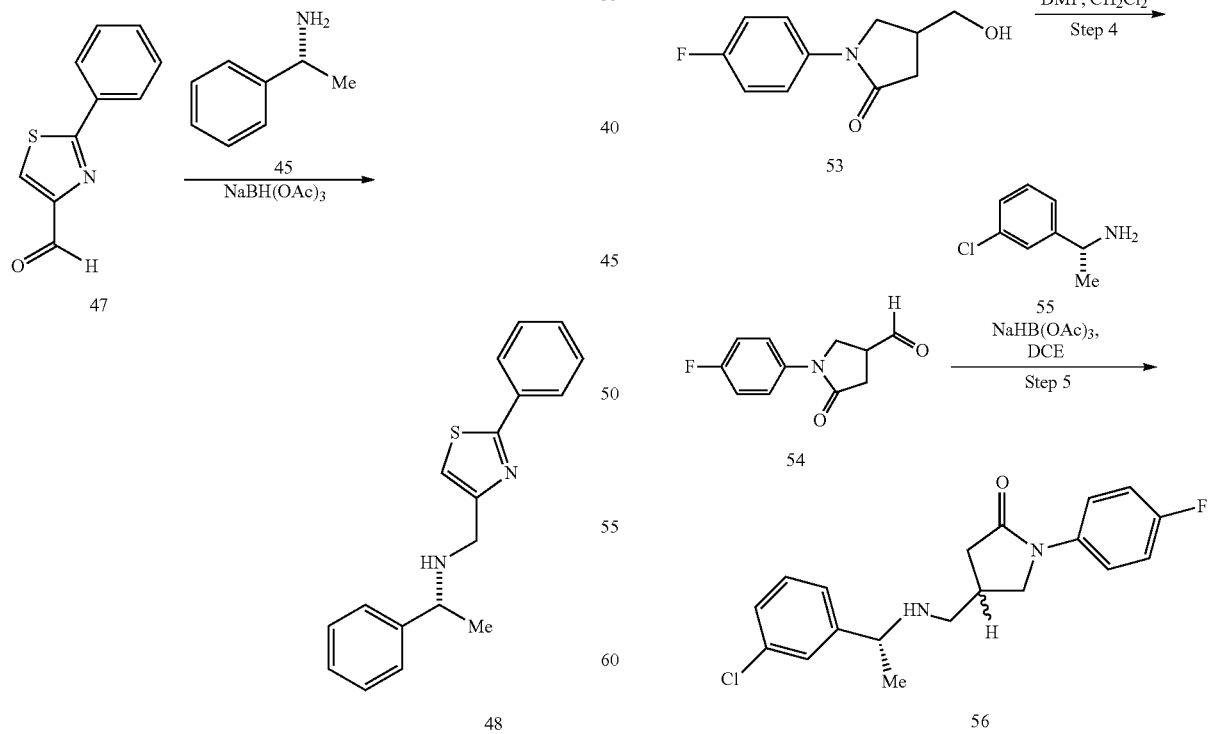

Step 1. A 250 mL round-bottomed flask was charged with 4-fluoroaniline 50 (12.8 g, 115 mmol) and 2-methylenesuccinic acid 49 (15.0 g, 115 mmol). The flask was fitted with a reflux condenser then heated at 170° C. Once at that temperature, heating was continued for 15 min. After that time, the molten mass was cooled to room temperature and water was added. The resulting precipitate was filtered then dissolved in 2 N NaOH. The solution was filtered again and the filtrate was acidified using concentrated HCl. The resulting precipitate was collected by filtration and dried at 70° C. under vacuum to give 1-(4-fluorophenyl)-5-oxopyrrolidine-3-carboxylic acid 51.

Step 2. To 1-(4-fluorophenyl)-5-oxopyrrolidine-3-carboxylic acid 51 was added 80 mL of $CH_2Cl_2$, 30 mL of MeOH, and 1.0 mL of concentrated $H_2SO_4$. After heating at reflux overnight, the mixture concentrated and triturated with water to give methyl 1-(4-fluorophenyl)-5-oxopyrrolidine-3-carboxylate 52.

Step 3. A 500 mL round-bottomed flask was charged with methyl 1-(4-fluorophenyl)-5-oxopyrrolidine-3-carboxylate 52 (7.50 g, 31.6 mmol), sodium borohydride (1.32 g, 34.8 mmol), and 100 mL of THF. After being heated to reflux, 15 mL of MeOH was slowly added. After 1 h at reflux, the reaction was concentrated, 100 mL of water was added, and the mixture was extracted with DCM. The combined extracts were dried and concentrated to give 1-(4-fluorophenyl)-4-(hydroxymethyl)pyrrolidin-2-one 53.

Step 4. A 500 mL round-bottomed flask was charged with 1-(4-fluorophenyl)-4-(hydroxymethyl)pyrrolidin-2-one 53 (6.01 g, 28.7 mmol), 100 mL of DCM, and Dess-Martin periodinane (DMP) (15.8 g, 57.3 mmol). After stirring at room temperature for 1.5 h, the reaction was quenched with saturated aqueous sodium thiosulfate and filtered. The layers were separated and the residue was purified by column chromatography on silica gel (10% to 90% EtOAc in hexanes) to give 1-(4-fluorophenyl)-5-oxopyrrolidine-3-carbaldehyde 54.

Step 5. A 20 mL vial was charged with sodium triacetoxyborohydride (1.0 g, 4.8 mmol), (R)-1-(3-chlorophenyl)ethanamine 55 (0.413 g, 2.7 mmol), 1-(4-fluorophenyl)-5-oxopyrrolidine-3-carbaldehyde 54 (0.500 g, 2.4 mmol), 10 mL of DCE, and 5 drops of AcOH. This mixture was stirred at room temperature overnight then quenched with saturated aqueous $NaHCO_3$. The mixture was extracted with DCM, dried, concentrated, and purified by column chromatography on silica gel (3% to 7% MeOH in DCM) to give 4-({[(1R)-1-(3-chlorophenyl)ethyl]amino}methyl)-1-(4-fluorophenyl)pyrrolidin-2-one 56 as a 1:1 mixture of diastereomers. Mass spectrum: calculated for $C_{19}H_{20}ClFN_2O$ 346.1; found 347.2 ($M^++1$).

Example 8

Synthesis of 1-(4-fluorophenyl)-4-({[(1R)-1-(1-naphthyl)ethyl]amino}methyl)pyrrolidin-2-one

57

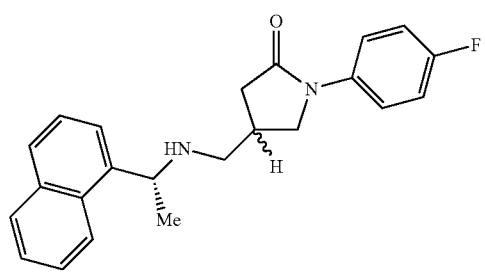

1-(4-Fluorophenyl)-4-({[(1R)-1-(1-naphthyl)ethyl]amino}methyl)pyrrolidin-2-one 57 was prepared as a 1:1 mixture of diastereomers using the same procedure given in Example 7 (Step 5) except substituting (R)-1-(3-chlorophenyl)ethanamine 55 for (R)-1-(naphthalen-1-yl)ethanamine 39. Mass spectrum: calculated for $C_{23}H_{23}FN_2O$ 362.2; found 363.3 ($M^++1$).

Example 9

Synthesis of (1R)-1-(3-chlorophenyl)-N-{[1-(4-fluorophenyl)pyrrolidin-3-yl]methyl}ethanamine

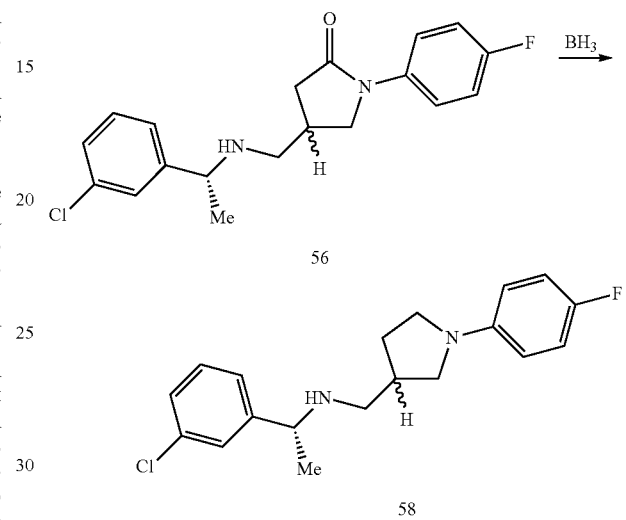

A 100 mL round-bottomed flask was charged with 4-({[(1R)-1-(3-chlorophenyl)ethyl]amino}methyl)-1-(4-fluorophenyl)pyrrolidin-2-one 56 (0.400 g, 1.0 mmol) as a 1:1 mixture of diastereomers and 10 mL of THF. To this solution was added $BH_3$·THF (1 M in THF, 5.2 mL, 5.2 mmol). The mixture was heated to reflux for 3 h then cooled to 0° C. The reaction was quenched with saturated aqueous $NaHCO_3$ and extracted with $CH_2Cl_2$. The extracts were dried and concentrated to give an oil, which was purified by column chromatography on silica gel (2% to 7% MeOH in DCM) to give (1R)-1-(3-chlorophenyl)-N-{[1-(4-fluorophenyl)pyrrolidin-3-yl]methyl}ethanamine 58 as a 1:1 mixture of diastereomers. Mass spectrum, calculated for $C_{19}H_{22}ClFN_2$ 332.1; found 333.2 ($M^++1$).

Example 10

Synthesis of (1R)-1-(1-naphthyl)-N-({1-[4-(trifluoromethyl)phenyl]-1H-pyrazol-3-yl}methyl)ethanamine

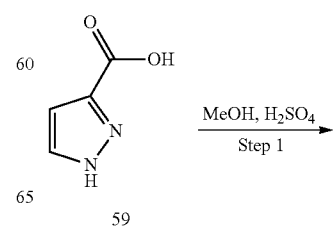

59

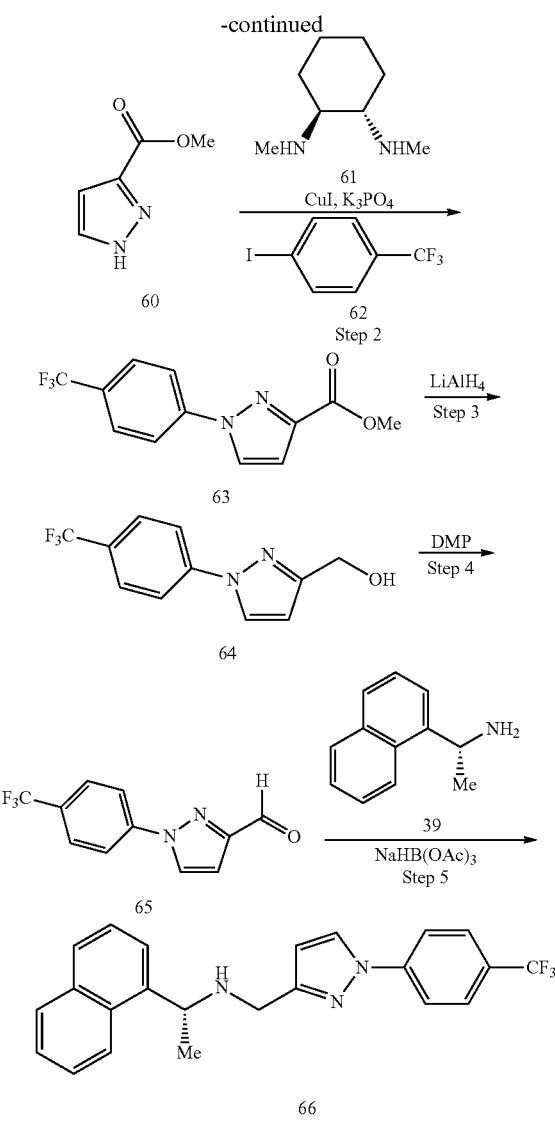

Step 1. A 500 mL round-bottomed flask was charged with 1H-pyrazole-3-carboxylic acid 59 (5.0 g, 45 mmol), 100 mL of MeOH, and 10 drops of concentrated sulfuric acid. This mixture was heated to reflux and heating was continued for 12 h. After cooling to room temperature, the solvent was removed and the residue was dissolved in EtOAc and saturated aqueous NaHCO₃. The layers were separated and the organic layer was dried and concentrated to give methyl 1H-pyrazole-3-carboxylate 60.

Step 2. A 30 mL pressure tube was charged with (1S,2S)—N1,N2-dimethylcyclohexane-1,2-diamine 61 (0.41 mL, 2.6 mmol), copper iodide (361 mg, 1.9 mmol), potassium phosphate (6.1 g, 29 mmol), 1-iodo-4-(trifluoromethyl)benzene 62 (3.2 g, 12 mmol), methyl 1H-pyrazole-3-carboxylate 60 (1.5 g, 12 mmol), and 15 mL of toluene. This mixture was heated at 110° C. for 16 h. After cooling to room temperature, the mixture was diluted with EtOAc and filtered. The filtrate was concentrated onto silica and purified by flash column chromatography on silica gel (0% to 3% MeOH in DCM) to give methyl 1-(4-(trifluoromethyl)phenyl)-1H-pyrazole-3-carboxylate 63.

Step 3. A 100 mL round-bottomed flask was charged with methyl 1-(4-(trifluoromethyl)phenyl)-1H-pyrazol-3-carboxylate 63 (0.800 g, 2.96 mmol) and 10 mL of THF. After being cooled to 0° C., lithium aluminum hydride (1.0 M solution in THF, 2.96 mL, 2.96 mmol) was added dropwise. After 1 h, the reaction was quenched with 0.5 mL of water, 0.5 mL of 1 M NaOH, and 1.5 mL of water (added in that order). The resulting precipitate was filtered and the filtrate concentrated to give (1-(4-(trifluoromethyl)phenyl)-1H-pyrazol-3-yl)methanol 64.

Step 4. A 100 mL round-bottomed flask was charged with (1-(4-(trifluoromethyl)phenyl)-1H-pyrazol-3-yl)methanol 64 (0.703 g, 2.90 mmol) and 10 mL CH₂Cl₂. To this solution was added Dess-Martin periodinane (1.60 g, 3.77 mmol). After stirring at room temperature for 30 min, the reaction was quenched with saturated aqueous sodium thiosulfate. The layers were separated and the organics were dried and concentrated. The concentrate was passed through a short pad of silica gel rinsing with 7:1 hexanes/EtOAc to give 1-(4-(trifluoromethyl)phenyl)-1H-pyrazole-3-carbaldehyde 65.

Step 5. A 20 mL vial was charged with 1-(4-(trifluoromethyl)phenyl)-1H-pyrazole-3-carbaldehyde 65 (0.200 g, 0.833 mmol), (R)-1-(naphthalen-1-yl)ethanamine 39 (0.171 g, 0.999 mmol), sodium triacetoxyborohydride (0.353 g, 1.67 mmol), 4 mL of DCE, and 3 drops of AcOH. This mixture was stirred overnight at room temperature and then quenched with saturated aqueous NaHCO₃. The mixture was extracted with DCM, dried, and concentrated. Purification by column chromatography on silica gel (10% to 50% EtOAc in hexanes) gave ((1R)-1-(1-naphthyl)-N-({1-[4-(trifluoromethyl)phenyl]-1H-pyrazol-3-yl}methyl)ethanamine 66. Mass spectrum, calculated for $C_{23}H_{20}F_3N_3$ 395.2; found 396.2 (M⁺+1).

Example 11

Synthesis of (1R)-1-(3-fluorophenyl)-N-({1-[4-(trifluoromethyl)phenyl]-1H-pyrazol-3-yl}methyl)ethanamine

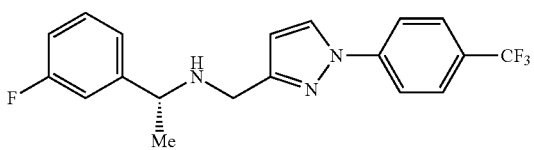

(1R)-1-(3-fluorophenyl)-N-({1-[4-(trifluoromethyl)phenyl]-1H-pyrazol-3-yl}methyl)ethanamine 67 was prepared using the same procedure given in Example 10 (Step 5) except substituting (R)-1-(naphthalen-1-yl)ethanamine 39 for (R)-1-(3-fluorophenyl)ethanamine. Mass spectrum: calculated for $C_{19}H_{17}F_4N_3$ 363.1; found 364.2 (M⁺+1).

Example 12

Synthesis of (1R)-1-(3-chlorophenyl)-N-({1-[4-(trifluoromethyl)phenyl]-1H-pyrazol-3-yl}methyl)ethanamine

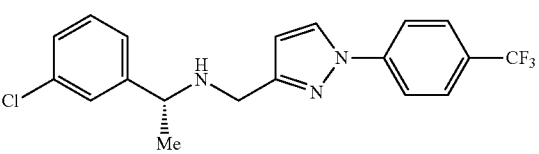

(1R)-1-(3-chlorophenyl)-N-({1-[4-(trifluoromethyl)phenyl]-1H-pyrazol-3-yl}methyl)ethanamine 68 was prepared using the same procedure given in Example 10 (Step 5) except substituting (R)-1-(naphthalen-1-yl)ethanamine 39 for (R)-1-(3-chlorophenyl)ethanamine 55. Mass spectrum: calculated for $C_{19}H_{17}ClF_3N_3$ 379.1; found 380.1 (M$^+$+1).

Example 13

Synthesis of (1R)—N-({5-methoxy-1-[4-(trifluoromethyl)phenyl]-1H-pyrazol-3-yl}methyl)-1-phenylethanamine

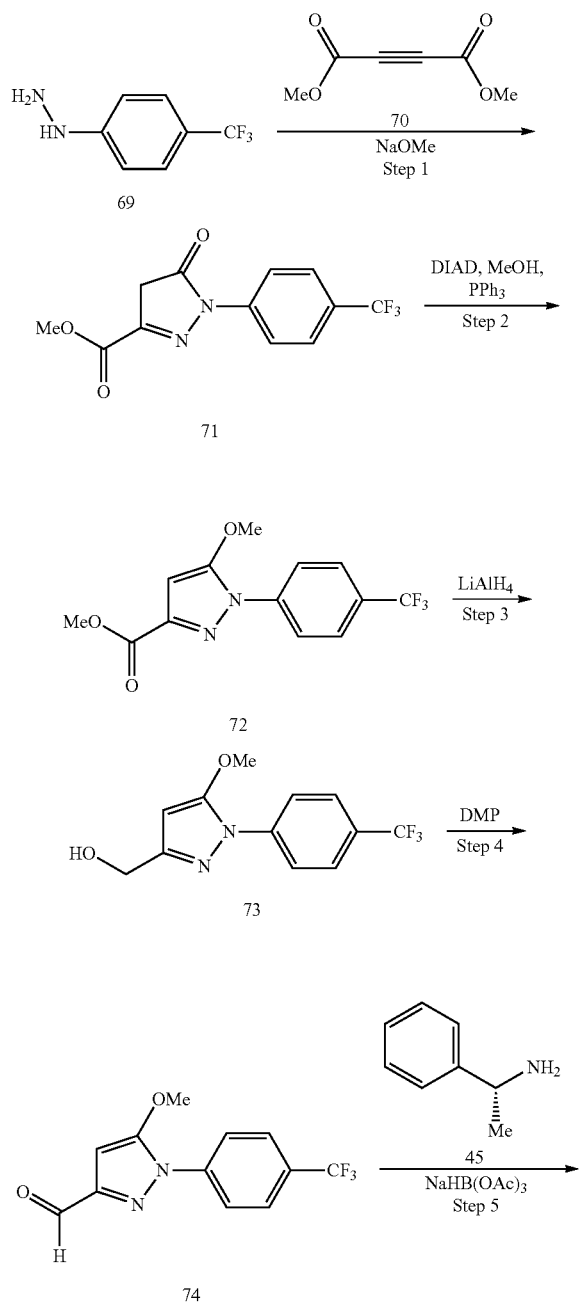

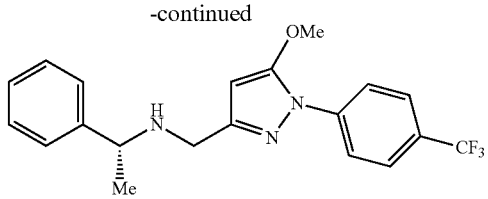

Step 1. A 500 mL round-bottomed flask was charged with dimethyl but-2-ynedioate 70 (6.0 g, 42 mmol) and 50 mL of ether. To this solution was added a solution of 1-(4-(trifluoromethyl)phenyl)hydrazine 69 (7.6 g, 43 mmol) in 100 mL of ether over 30 min. After stirring at room temperature for 30 min, the reaction was concentrated and redissolved in MeOH (200 mL). The solution was added dropwise over 1 h to a NaOMe solution (made from sodium metal (3.9 g, 169 mmol) in 200 mL of MeOH). This mixture was stirred at room temperature for 1.5 h, the MeOH was removed, 100 mL of 5 N HCl was added, and the precipitate was collected by filtration. The solid was triturated with $CH_2Cl_2$ to give methyl 5-oxo-1-(4-(trifluoromethyl)phenyl)-4,5-dihydro-1H-pyrazole-3-carboxylate 71.

Step 2. A 500 mL round-bottomed flask was charged with triphenylphosphine (6.9 g, 26 mmol), methyl 5-oxo-1-(4-(trifluoromethyl)phenyl)-4,5-dihydro-1H-pyrazole-3-carboxylate 71 (5.0 g, 17 mmol), MeOH (0.88 mL, 22 mmol), and 200 mL of benzene. After cooling to 0° C., diisopropyl azodicarboxylate (DIAD) (5.2 mL, 26 mmol) was added dropwise. The mixture was stirred at room temperature for 18 h, then diluted with water and extracted with $CH_2Cl_2$. The combined extracts were dried and concentrated to give an oil that was purified by column chromatography on silica gel (5% to 40% EtOAc in hexanes) to give methyl 5-methoxy-1-(4-(trifluoromethyl)phenyl)-1H-pyrazole-3-carboxylate 72.

Step 3. A 100 mL round-bottomed flask was charged with methyl 5-methoxy-1-(4-(trifluoromethyl)phenyl)-1H-pyrazole-3-carboxylate 72 (5.20 g, 17 mmol) and 100 mL of THF. After being cooled to 0° C., lithium aluminum hydride (1.0 M solution in THF, 17 mL, 17 mmol) was added dropwise. After 1 h, the reaction was quenched with 0.5 mL of water, 0.5 mL of 1 M NaOH, and 1.5 mL of water (added in that order). The resulting precipitate was filtered and the filtrate was concentrated to give (5-methoxy-1-(4-(trifluoromethyl)phenyl)-1H-pyrazol-3-yl)methanol 73.

Step 4. A 250 mL round-bottomed flask was charged with (5-methoxy-1-(4-(trifluoromethyl)phenyl)-1H-pyrazol-3-yl)methanol 73 (4.60 g, 16.9 mmol) and 50 mL of $CH_2Cl_2$. To this solution was added Dess-Martin periodinane (8.96 g, 21.1 mmol) and the mixture was stirred at room temperature for 1.5 h. The reaction mixture was quenched with saturated aqueous $Na_2S_2O_3$, extracted with $CH_2Cl_2$, dried, and concentrated. Purification by via column chromatography on silica gel (0% to 20% EtOAc in hexanes) to give 5-methoxy-1-(4-(trifluoromethyl)phenyl)-1H-pyrazole-3-carbaldehyde 74.

Step 5. A 20 mL vial was charged with (R)-1-phenylethanamine 45 (0.135 g, 1.11 mmol), 5-methoxy-1-(4-(trifluoromethyl)phenyl)-1H-pyrazole-3-carbaldehyde 74 (0.200 g, 0.740 mmol), 5 mL of DCE, 3 drops of concentrated AcOH, and sodium triacetoxyborohydride (0.314 g, 1.48 mmol). The reaction mixture was stirred at room temperature overnight. The reaction mixture was quenched with 10 mL of saturated aqueous $NaHCO_3$ and the mixture was extracted with $CH_2Cl_2$. The combined extracts were dried and concentrated. Purification via column chromatography on silica gel (1% to 6% MeOH in DCM) gave (1R)—N-({5-methoxy-1-[4-(trifluoromethyl)phenyl]-1H-pyrazol-3-yl}methyl)-1-phenylethanamine 75. Mass spectrum: calculated for $C_{20}H_{20}F_3N_3O$ 375.2; found 376.2 ($M^++1$).

Example 14

Synthesis of (1R)-1-(3-fluorophenyl)-N-({5-methoxy-1-[4-(trifluoromethyl)phenyl]-1H-pyrazol-3-yl}methyl)ethanamine

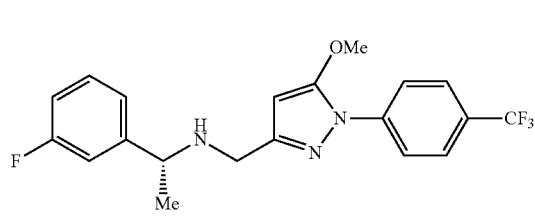

(1R)-1-(3-fluorophenyl)-N-({5-methoxy-1-[4-(trifluoromethyl)phenyl]-1H-pyrazol-3-yl}methyl)ethanamine 76 was prepared using the same procedure given in Example 13 (Step 5) except substituting (R)-1-phenylethanamine 45 for (R)-1-(3-fluorophenyl)ethanamine. Mass spectrum: calculated for $C_{20}H_{19}F_4N_3O$ 393.1; found 394.2 ($M^++1$).

Example 15

Synthesis of (1R)-1-(3-chlorophenyl)-N-({5-methoxy-1-[4-(trifluoromethyl)phenyl]-1H-pyrazol-3-yl}methyl)ethanamine

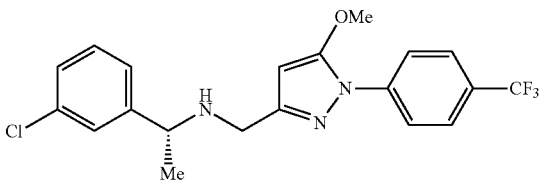

(1R)-1-(3-chlorophenyl)-N-({5-methoxy-1-[4-(trifluoromethyl)phenyl]-1H-pyrazol-3-yl}methyl)ethanamine 77 was prepared using the same procedure given in Example 13 (Step 5) except substituting (R)-1-phenylethanamine 45 for (R)-1-(3-chlorophenyl)ethanamine 55. Mass spectrum: calculated for $C_{20}H_{19}ClF_3N_3O$ 409.1; found 410.2 ($M^++1$).

Example 16

The compounds shown in Table 5 were prepared by either procedure 1 or procedure 2 shown below. Representative procedures for steps 1-6 are given below. Aldehyde 78 and ester 83 were prepared using the procedures shown in Example 13 except substituting 1-(4-(trifluoromethyl)phenyl)hydrazine 69 for the corresponding arylhydrazines.

1-(6-(Trifluoromethyl)pyridin-3-yl)hydrazine was prepared as follows: A 250-mL round bottomed flask containing a solution of 6-(trifluoromethyl)pyridin-3-amine (5.76 g, 35.5 mmol) in 50 mL of 4 N HCl was cooled to 0° C. in an ice bath and a solution of sodium nitrite (2.57 g, 37.3 mmol) in 5 mL of water was added dropwise. The reaction mixture was stirred at 0° C. for 30 min and added to a solution of tin(II) chloride dihydrate (16.8 g, 74.6 mmol) in 60 mL of 4 N HCl at 80° C. The reaction mixture was stirred at 80° C. for 3 h, cooled to room temperature, and made basic by the addition of 10 N NaOH. The aqueous phase was extracted with EtOAc (4×). The combined organic extracts were concentrated and the crude material was absorbed onto silica gel. Purification by flash column chromatography on silica gel (10% to 100% EtOAc in hexanes) gave 1-(6-(trifluoromethyl)pyridin-3-yl)hydrazine.

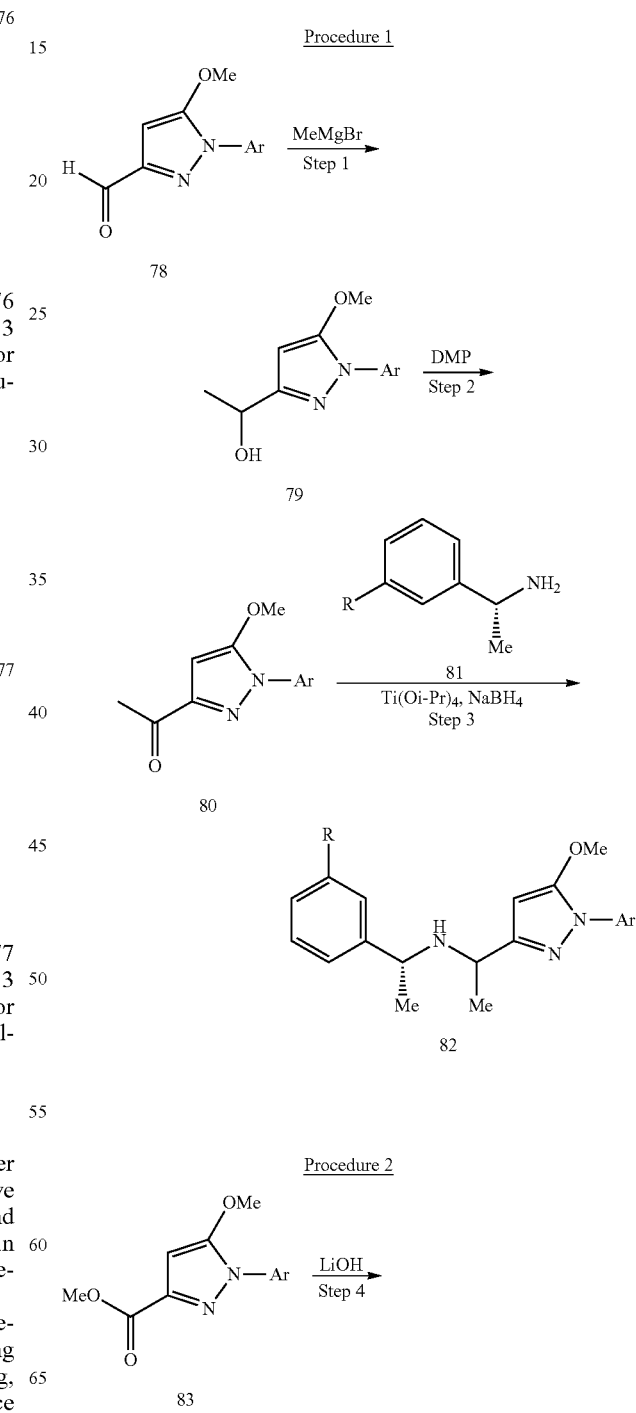

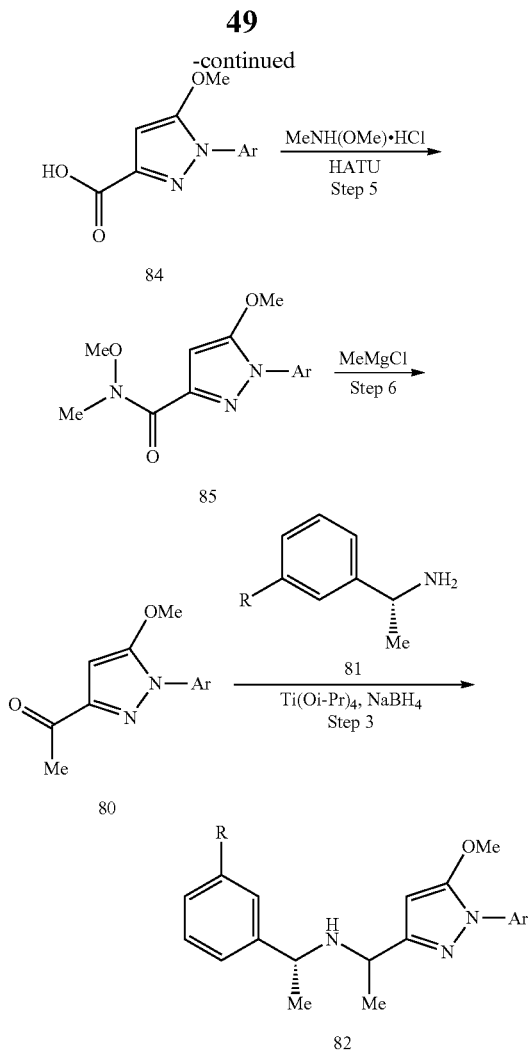

Step 1. A 250 mL round-bottom flask was charged with aldehyde 78 (6.1 mmol) and 15 mL of THF. After being cooled to 0° C., methylmagnesium bromide (1.4 M solution in toluene/tetrahydrofuran (75:25), 5.5 mL, 7.6 mmol) was added and the reaction was stirred at 0° C. for 1 h. The reaction mixture was quenched with saturated aqueous NH₄Cl, extracted with DCM, dried, and concentrated to give alcohol 79.

Step 2. Alcohol 79 from the previous step was dissolved in CH₂Cl₂ and Dess-Martin periodinane (3.9 g, 9.2 mmol) was added. After 30 min, the reaction was quenched with saturated aqueous Na₂S₂O₃ and extracted with CH₂Cl₂. The extracts were dried and concentrated. Purification via column chromatography on silica gel (EtOAc in hexanes) gave ketone 80.

Step 3. A 100 mL round-bottom flask was charged with ketone 80 (1.1 mmol), primary amine 81 (1.3 mmol), and 15 mL of THF. To this solution was added titanium isopropoxide (2.1 mmol). The reaction was stirred at 40° C. for 24 h, cooled to −78° C., and a solution of NaBH₄ (2.1 mmol) in 5 mL of MeOH was added. After stirring at −78° C. for 1 h, the reaction mixture was quenched with concentrated NH₄OH and filtered. The filtrate was concentrated and purified via column chromatography on silica gel (EtOAc in hexanes) to give amine 82.

Step 4. Ester 83 (47 mmol) was dissolved in 300 mL of THF and 150 mL of water. To this solution was added LiOH (232 mmol). After stirring for 3 h at room temperature, the reaction was diluted with water and washed with CH₂Cl₂ (3×150 mL). The aqueous layer was acidified with concentrated HCl and extracted with EtOAc. The organic phase was dried and concentrated to give carboxylic acid 84.

Step 5. A 1 L round-bottomed flask was charged with carboxylic acid 84 (42 mmol), N,O-dimethylhydroxylamine hydrochloride (44 mmol), N,N-diisopropylethylamine (84 mmol), 200 mL of DMF, and O-(7-azabenzotriazol-1-yl)-N,N,N',N'-tetramethyluronium hexafluorophosphate (HATU) (42 mmol). The reaction mixture was stirred overnight at room temperature and diluted with water. The aqueous phase was extracted with EtOAc, dried, and concentrated to give amide 85.

Step 6. Amide 85 from the previous step was dissolved in THF (300 mL) and methylmagnesium chloride (51 mmol) was added at 0° C. After stirring for 30 min, the reaction was quenched with 1 M HCl and extracted with ether, dried, and concentrated. Purification by trituration with hexanes or column chromatography on silica gel (EtOAc in hexanes) gave 80.

TABLE 5

| Comp | Structure | Name | m/z | dr |
|---|---|---|---|---|
| 86 | 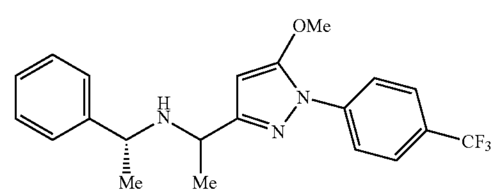 | 1-{5-methoxy-1-[4-(trifluoromethyl)phenyl]-1H-pyrazol-3-yl}-N-[1R)-1-phenylethyl]ethanamine | 390.2 | >20:1 |
| 87 | 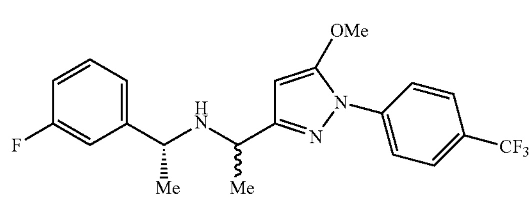 | (1R)-1-(3-fluorophenyl)-N-(1-{5-methoxy-1-[4-(trifluoromethyl)phenyl]-1H-pyrazol-3-yl}ethyl)ethanamine | 408.2 | 13:1 |

TABLE 5-continued

| Comp | Structure | Name | m/z | dr |
|---|---|---|---|---|
| 88 | 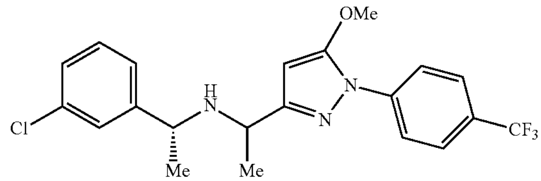 | (1R)-1-(3-chlorophenyl)-N-(1-{5-methoxy-1-[4-(trifluoromethyl)phenyl]-1H-pyrazol-3-yl}ethyl)ethanamine | 424.2 | >20:1 |
| 89 | 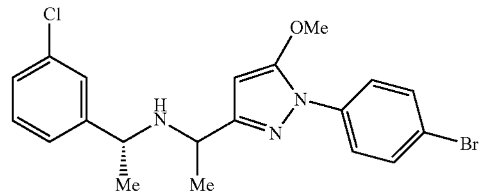 | 1-[1-(4-bromophenyl)-5-methoxy-1H-pyrazol-3-yl]-N-[(1R)-1-(3-chlorophenyl)ethyl]ethanamine | 434.1 | >20:1 |
| 90 | 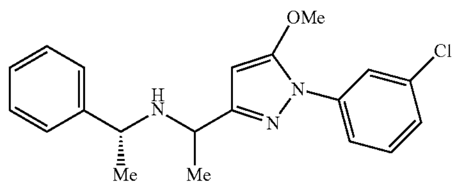 | 1-[1-(3-chlorophenyl)-5-methoxy-1H-pyrazol-3-yl]-N-(1R)-1-phenylethyl]ethanamine | 356.9 | >20:1 |
| 91 | 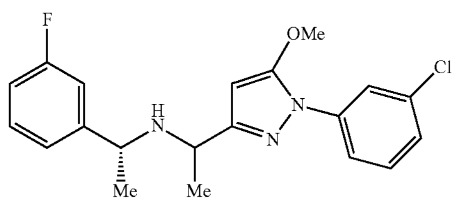 | 1-[1-(3-chlorophenyl)-5-methoxy-1H-pyrazol-3-yl]-N-[(1R)-1-(3-fluorophenyl)ethyl]ethanamine | 374.9 | >20:1 |
| 92 | 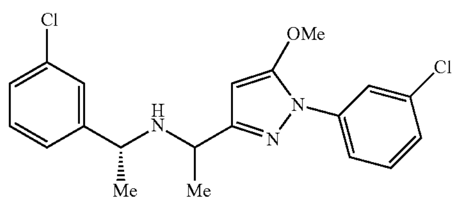 | (1R)-1-(3-chlorophenyl)-N-{1-[1-(3-chlorophenyl)-5-methoxy-1H-pyrazol-3-yl]ethyl}ethanamine | 391.3 | >20:1 |
| 93 | 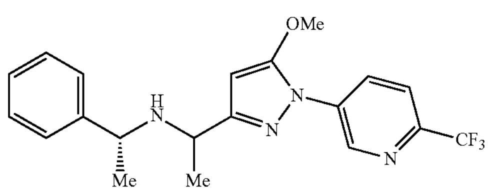 | 1-{5-methoxy-1-[6-(trifluoromethyl)pyridin-3-yl]-1H-pyrazol-3-yl}-N-[(1R)-1-phenylethyl]ethanamine | 391.4 | >20:1 |
| 94 | 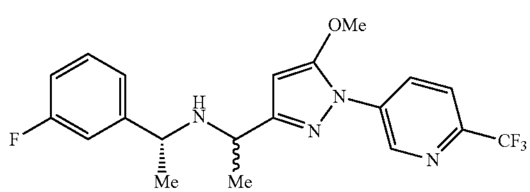 | (1R)-1-(3-fluorophenyl)-N-(1-{5-methoxy-1-[6-(trifluoromethyl)pyridin-3-yl]-1H-pyrazol-3-yl}ethyl)ethanamine | 409.4 | 10:1 |
| 95 | 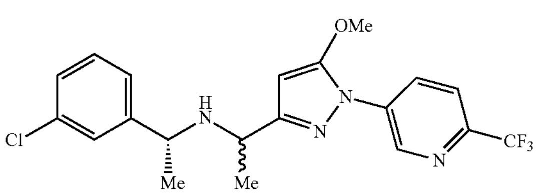 | (1R)-1-(3-chlorophenyl)-N-(1-{5-methoxy-1-[6-(trifluoromethyl)pyridin-3-yl]-1H-pyrazol-3-yl}ethyl)ethanamine | 425.9 | 10:1 |

Example 17

Synthesis of 4-[3-(1-{[(1R)-1-(3-chlorophenyl)ethyl]amino}ethyl)-5-methoxy-1H-pyrazol-1-yl]benzonitrile

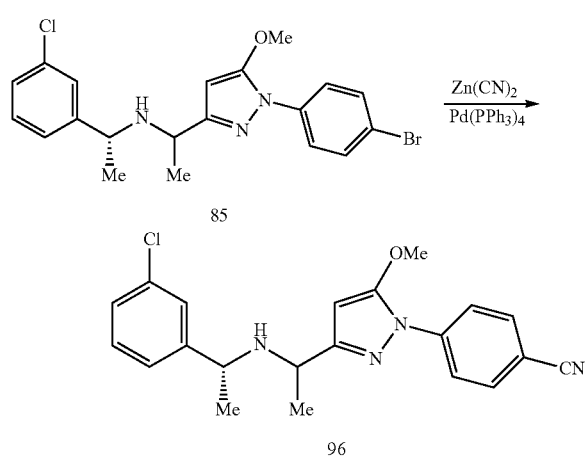

A 20 mL vial was charged with Pd(PPh$_3$)$_4$ (0.159 g, 0.138 mmol), zinc cyanide (0.243 g, 2.07 mmol), 3 mL of DMF, and 1-[1-(4-bromophenyl)-5-methoxy-1H-pyrazol-3-yl]-N—[(1R)-1-(3-chlorophenyl)ethyl]ethanamine 85 (0.600 g, 1.38 mmol) as a >20:1 mixture of diastereomers. The reaction mixture was heated to 100° C. After 3 d, an additional 10 mol % of Pd(PPh$_3$)$_4$ and 2 equivalents of ZnCN$_2$ were added. The reaction mixture was heated in a microwave to 180° C. for 15 min. The reaction mixture was cooled to room temperature, dissolved in EtOAc, washed with water and brine, dried, and concentrated. Purification by flash column chromatography on silica gel (2% MeOH in DCM) gave 4-43-(1-{[(1R)-1-(3-chlorophenyl)ethyl]amino}ethyl)-5-methoxy-1H-pyrazol-1-yl]benzonitrile 96 as a >20:1 mixture of diastereomers. Mass spectrum: calculated for C$_2$H$_{21}$ClN$_4$O 380.1; found 381.2 (M$^+$+1).

Example 18

The compounds in Table 6 were prepared as a >20:1 mixture of diastereomers by the sequence shown below using the procedures given in Example 16.

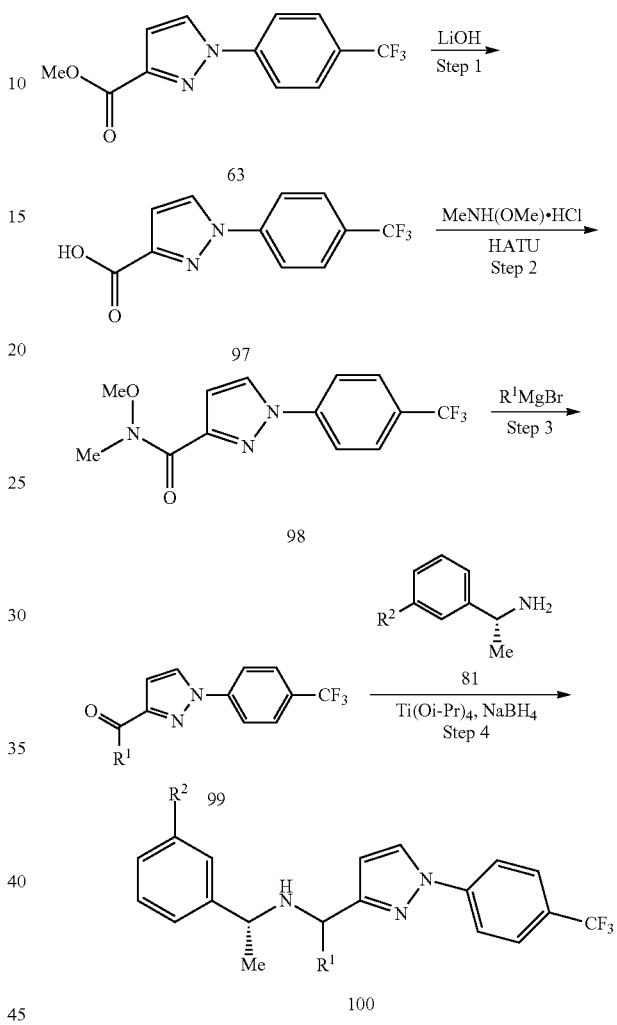

TABLE 6

| Comp | Structure | Name | m/z |
|---|---|---|---|
| 101 | 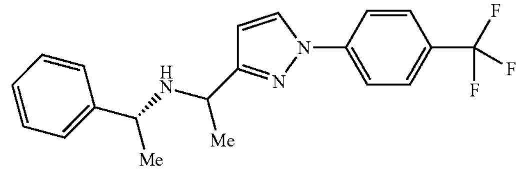 | (1R)-1-phenyl-N-(1-{1-[4-(trifluoromethyl)phenyl]-1H-pyrazol-3-yl}ethyl)ethanamine | 360.4 |
| 102 | 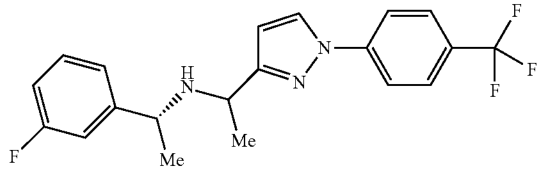 | (1R)-1-(3-fluorophenyl)-N-(1-{1-[4-(trifluoromethyl)phenyl]-1H-pyrazol-3-yl}ethyl)ethanamine | 378.4 |

TABLE 6-continued

| Comp | Structure | Name | m/z |
|---|---|---|---|
| 103 | 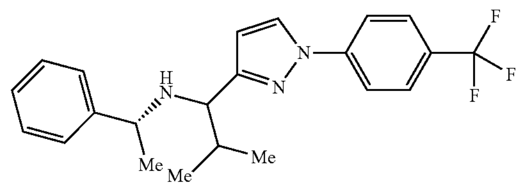 | 2-methyl-N-[(1R)-1-phenylethyl]-1-{1-[4-(trifluoromethyl)phenyl]-1H-pyrazol-3-yl}propan-1-amine | 388.4 |
| 104 | 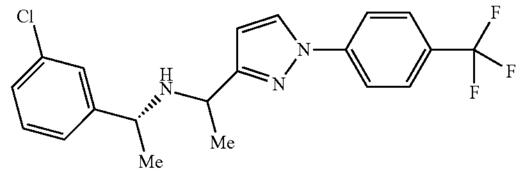 | (1R)-1-(3-chlorophenyl)--(1-{1-[4-(trifluoromethyl)phenyl]-1H-pyrazol-3-yl}ethyl)ethanamine | 394.8 |
| 105 | 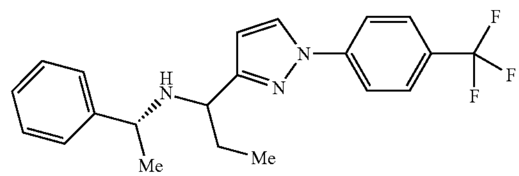 | N-[(1R)-1-phenylethyl]-1-{1-[4-(trifluoromethyl)phenyl]-1H-pyrazol-3-yl}propan-1-amine | 374.4 |

Example 19

Biological Activity

The activities of the compounds of the present invention on calcium receptors were measured. In one aspect, the measurement was performed in accordance with the method described in Example 4 of International Publication No. WO 96/12697.

A 4.0-kb NotI-HindIII fragment of the human parathyroid cell $Ca^{2+}$ receptor (hPCaR) cDNA was subcloned into the mammalian expression vector pCEP4 (Invitrogen) containing the hygromycin-resistant gene as a selectable marker. This plasmid was transfected into HEK 293 cells by calcium phosphate precipitation. Transfected cells were grown in Dulbecco's modified Eagle's medium containing 10% fetal bovine serum and hygromycin (200 g/mL). Hygromycin-resistant colonies were subcloned and assayed for hPCaR mRNA by solution hybridization using a $^{32}$P-labeled RNA probe complementary to the (4.0 kb) hPCaR sequence (Garrett, et al., J. Biol. Chem. 270, 12919-12925 (1995)). Clone 7 was used to assess the effects of compounds on $[Ca^{2+}]_i$. This stably transfected cell line is termed HEK 293 4.0-7. For measurements of $[Ca^{2+}]_i$, the cells were recovered from tissue culture flasks by brief treatment with Versene (Invitrogen; containing 0.2 g/L EDTA•4Na in phosphate-buffered saline) and then seeded in collagen coated 384-well plates (BD Biosciences) at 20K cells per well in the growth media (same as above). Cells were grown in 37° C. TC incubator overnight. Then, the media was discarded and cells were loaded with 1× dye from Ca2+ Assay Kit I (BD Biosciences) in parathyroid cell buffer (126 mM NaCl, 4 mM KCl, 1 mM $MgSO_4$, 0.7 mM $K_2HPO_4$/$KH_2PO_4$, 20 mM HEPES.NaOH (pH 7.45)) containing 0.5% BSA and 1 mM $CaCl_2$. Cells were loaded at room temperature for 90 minutes. Each test compound was added to the cells and the fluorescence was recorded by using excitation and emission wavelengths of 485 and 530 nm, respectively.

The compounds of the invention were tested according to the procedure described above and found to have an $EC_{50}$ of 5 μM or less.

In Vivo Measurements

Male Sprague-Dawley rats weighing 250-400 g were given free access to food and water. Unanesthetized rats were gavaged with an 18-gauge balled needle at a volume between 0.5 and 1 ml. Compounds were formulated in 20% captisol in water at pH 7.0 or 2% hydroxypropyl methylcellulose (HPMC)/1% Tween 80/5% Captisol in water pH 2.0. Calcimimetics were administered at various doses covering the following range 0.03-30 mg/kg in 20% captisol. Vehicle-treated rats received one of the above two vehicles at the maximum volume (0.5-1 ml) used for the calcimimetics. Each rat was bled at time 0 (pre-calcimimetic or vehicle administration) and at various times (1, 2, 4, 8 and 24 h) after oral gavage of calcimimetic or vehicle.

For measurements of blood-ionized $Ca^{2+}$ levels, blood (50 μl) was collected from the orbital sinus of anesthetized rats (3% isoflurane in $O_2$) with heparinized capillary tubes. Blood samples were analyzed within seconds of collection using a Rapidlab 348 Blood Gas Analyzer (Bayer HealthCare LLC Diagnostic Division; Tarrytown, N.Y.).

For measurements of serum PTH, phosphorus, a nonheparinized capillary tube was inserted into the orbital sinus and blood (0.5 ml) was collected into SST (clot activator) brand blood tubes. Blood samples were allowed to clot for 15-30 min and centrifuged (3000 rpm; Sorvall RT 600B) at 4° C. Serum was removed and stored below 0° C. until assayed. Serum PTH levels were quantified according to the vendor's instructions using rat PTH immunoradiometric assay kits (Immutopics, San Clemente, Calif.) or rat bioactive intact PTH elisa kit (Immutopics, San Clemente, Calif.). Serum phosphorus levels were determined using a blood chemistry analyzer (AU 400; Olympus, Melville, N.Y.).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound selected from the group consisting of:
- (1R)—N-(1H-imidazol-5-ylmethyl)-1-(1-naphthyl)ethanamine,
- (1R)-1-(3-methoxyphenyl)-N-[(1-methyl-1H-pyrrol-2-yl)methyl]ethanamine,
- (1R)—N-[(1-methyl-1H-pyrrol-2-yl)methyl]-1-(1-naphthyl)ethanamine,
- (1R)-1-(1-naphthyl)-N-(1H-pyrrol-2-ylmethyl)ethanamine,
- (1R)-1-(3-methoxyphenyl)-N-{[1-(phenylsulfonyl)-1H-pyrrol-2-yl]methyl}ethanamine,
- (1R)-1-(1-naphthyl)-N-{[1-(phenylsulfonyl)-1H-pyrrol-2-yl]methyl}ethanamine,
- (1R)-1-(3-methoxyphenyl)-N-(1H-pyrrol-2-ylmethyl)ethanamine,
- (1R)-1-(3-methoxyphenyl)-N-(1,3-thiazol-2-ylmethyl)ethanamine,
- (1R)—N-((4-chloro-1-methyl-1H-pyrazol-3-yl)methyl)-1-(3-(methyloxy)phenyl)ethanamine,
- (1R)—N-((4-chloro-1-methyl-1H-pyrazol-3-yl)methyl)-1-(1-naphthalenyl)ethanamine,
- (1R)-1-(3-(methyloxy)phenyl)-N-((2-phenyl-1H-imidazol-4-yl)methyl)ethanamine,
- (1R)-1-(1-naphthalenyl)-N-((2-phenyl-1H-imidazol-4-yl)methyl)ethanamine,
- (1R)-1-phenyl-N-((2-phenyl-1H-imidazol-4-yl)methyl)ethanamine,
- (1R)—N-((3,5-dimethyl-1-phenyl-1H-pyrazol-4-yl)methyl)-1-(3-(methyloxy)phenyl)ethanamine,
- (1R)—N-((3,5-dimethyl-1-phenyl-1H-pyrazol-4-yl)methyl)-1-(4-methylphenyl)ethanamine,
- (1R)—N-((3,5-dimethyl-1-phenyl-1H-pyrazol-4-yl)methyl)-1-(1-naphthalenyl)ethanamine,
- (1R)—N-((3,5-dimethyl-1-phenyl-1H-pyrazol-4-yl)methyl)-1-phenylethanamine,
- (1R)-1-(4-(methyloxy)phenyl)-N-((5-methyl-3-phenyl-4-isoxazolyl)methyl)ethanamine,
- (1R)—N-((5-methyl-3-phenyl-4-isoxazol)ypmethyl)-1-(1-naphthalenyl)ethanamine,
- (1R)—N-((5-methyl-3-phenyl-4-isoxazol)ypmethyl)-1-phenylethanamine,
- (1R)-1-(3-(methyloxy)phenyl)-N-((3-phenyl-1H-pyrazol-4-yl)methyl)ethanamine,
- (1R)-1-(4-(methyloxy)phenyl)-N-((3-phenyl-1H-pyrazol-4-yl)methyl)ethanamine,
- (1R)-1-(1-naphthalenyl)-N-((3-phenyl-1H-pyrazol-4-yl)methyl)ethanamine,
- (1R)-1-phenyl-N-((3-phenyl-1H-pyrazol-4-yl)methyl)ethanamine,
- (1R)—N-(1H-imidazol-2-ylmethyl)-1-(4-methylphenyl)ethanamine,
- (1R)—N-(1H-imidazol-2-ylmethyl)-1-(1-naphthalenyl)ethanamine,
- (1R)—N-((2-ethyl-4-methyl-1H-imidazol-5-yl)methyl)-1-(1-naphthalenyl)ethanamine,
- (1R)—N-((2-(4-chlorophenyl)-1,3-thiazol-4-yl)methyl)-1-(4-methylphenyl)ethanamine,
- (1R)—N-((2-(4-chlorophenyl)-1,3-thiazol-4-yl)methyl)-1-(1-naphthalenyl)ethanamine,
- (1R)—N-((2-(4-chlorophenyl)-1,3-thiazol-4-yl)methyl)-1-(2-naphthalenyl)ethanamine,
- (1R)-1-(1-naphthalenyl)-N-((2-phenyl-1,3-thiazol-4-yl)methyl)ethanamine,
- (1R)—N-((3-(4-(1,1-dimethylethyl)phenyl)-1,2,4-oxadiazol-5-yl)methyl)-1-(4-methylphenyl)ethanamine,
- (1R)—N-((3-(4-(1,1-dimethylethyl)phenyl)-1,2,4-oxadiazol-5-yl)methyl)-1-(2-naphthalenyl)ethanamine,
- (1R)-1-(1-naphthalenyl)-N-((1-phenyl-1H-pyrazol-5-yl)methyl)ethanamine,
- 1-(4-fluorophenyl)-4-({[(1R)-1-(1-naphthyl)ethyl]amino}methyl)pyrrolidin-2-one,
- 4-({[(1R)-1-(3-chlorophenyl)ethyl]amino}methyl)-1-(4-fluorophenyl)pyrrolidin-2-one,
- (1R)—N-[(5-chloro-1-methyl-4-phenyl-1H-imidazol-2-yl)methyl]-1-phenylethanamine,
- (1R)-1-phenyl-N-[(2-phenyl-1,3-thiazol-4-yl)methyl]ethanamine,
- (1R)-1-(3-chlorophenyl)-N-{[1-(4-fluorophenyl)pyrrolidin-3-yl]methyl}ethanamine,
- (1R)-1-(1-naphthyl)-N-({1-4-(trifluoromethyl)phenyl)-1H-pyrazol-3-yl}methyl)ethanamine,
- (1R)-1-(3-fluorophenyl)-N-({1-[4-(trifluoromethyl)phenyl]-1H-pyrazol-3-yl}methyl)ethanamine,
- (1R)-1-(3-chlorophenyl)-N-({1-[4-(trifluoromethyl)phenyl]-1H-pyrazol-3-yl}methyl)ethanamine,
- 1-{5-methoxy-1-[4-(trifluoromethyl)phenyl]-1H-pyrazol-3-yl}-N-[(1R)-1-phenylethylethanamine,
- (1R)-1-(3-fluorophenyl)-N-(1-{5-methoxy-1-[4-(trifluoromethyl)phenyl]-1H-pyrazol-3-Yl}ethyl)ethanamine,
- (1R)-1-(3-chlorophenyl)-N-{1-[1-(3-chlorophenyl)-5-methoxy-1H-pyrazol-3-yl]ethyl}ethanamine,
- 1-[1-(3-chlorophenyl)-5-methoxy-1H-pyrazol-3-yl]-N-[(1R)-1-(3-fluoropheny)ethyl]ethanamine,
- 1-[1-(3-chlorophenyl)-5-methoxy-1H-pyrazol-3-yl]-N-[(1R)-1-phenylethyl]ethanamine,
- (1R)-1-(3-chlorophenyl)-N-(1-{5-methoxy-1-[4-(trifluoromethyl)phenyl]-1H-pyrazol-3-yl }ethyl)ethanamine,
- 1-[1-(4-bromophenyl)-5-methoxy-1H-pyrazol-3-yl]-N-(1R)-1-(3-chlorophenypethyl)ethyl]ethanamine,
- 4-[3-(1{[(1R)-1-(3-chlorophenyl)ethyl]amino}ethyl)-5-methoxy- 1H-pyrazol-1-yl]benzonitrile,
- 1-{5-methoxy-1-[6-(trifluoromethyl)pyridin-3-yl]-1H-pyrazol-3-yl}-N-[(1R)-1-phenylethyl]ethanamine,
- (1R)-1-(3-fluorophenyl)-N-(1-(5-methoxy-1-[6-(trifluoromethyl)pyridin-3-yl)-1H-pyrazol-3-yl)ethyl)ethanamine,
- (1R)-1-(3-chlorophenyl)-N-(1-5-methoxy-1-[6-(trifluoromethyl)pyridine-3-yl]-1H-pyrazol-3-yl)ethyl)ethanamine,
- (1R)-1-phenyl-N-(1-{1-[4-(trifluoromethyl)phenyl]-1H-pyrazol-3-yl}ethyl)ethanamine,
- (1R)-1-(3-fluorophenyl)-N-(1-{1-[4-(trifluoromethyl)phenyl]-1H-pyrazol-3-yl}ethyl)ethanamine,
- 2-methyl-N-[(1R)-1-phenylethyl]-1-{1-[4-(trifluoromethyl)phenyl]-1H-pyrazol-3-yl}propan-1-amine,
- (1R)-1-(3-chlorophenyl)-N-((1R)-1-(1-(4-(trifluoromethyl)phenyl)-1H-pyrazol-3-yl)ethyl)ethanamine, and
- N-[(1R)-1-phenylethyl]-1-{1-[4-(trifluoromethyl)phenyl]-1H-pyrazol-3-yl}propan-1-amine, or a pharmaceutically acceptable salt thereof.

2. The compound of claim 1 selected from the group consisting of:
- (1R)-1-(3-methoxyphenyl)-N-(1,3-thiazol-2-ylmethyl)ethanamine,
- (1R)-1-(4-(methyloxy)phenyl)-N-((5-methyl-3-phenyl-4-isoxazolypmethyl)ethanamine,
- (1R)—N-((5-methyl-3-phenyl-4-isoxazoly)methyl)-1-(1-naphthalenyl)ethanamine,
- (1R)—N-((5-methyl-3-phenyl-4-isoxazoly)methyl)-1-phenylethanamine, (1R)—N-((2-(4-chlorophenyl)-1,3-thiazol-4-yl)methyl)-1-(4-methylphenyl)ethanamine,
(1R)—N-((2-(4-chlorophenyl)-1,3-thiazol-4-yl)methyl)-1-(1-naphthalenyl)ethanamine,
(1R)—N-((2-(4-chlorophenyl)-1,3-thiazol-4-yl)methyl)-1-(2-naphthalenyl)ethanamine,
(1R)-1-(1-naphthalenyl)-N-((2-phenyl-1,3-thiazol-4-yl)methyl)ethanamine,
(1R)—N-((3-(4-(1,1-dimethylethyl)phenyl)-1,2,4-oxadiazol-5-yl)methyl)-1-(4-methylphenyl)ethanamine,
(1R)—N-((3-(4-(1,1-dimethylethyl)phenyl)-1,2,4-oxadiazol-5-yl)methyl)-1-(2-naphthalenyl)ethanamine, and
(1R)-1-phenyl-N-[(2-phenyl-1,3-thiazol-4-yl)methyl]ethanamine, or a pharmaceutically acceptable salt thereof.

3. A pharmaceutical composition comprising the compound of claim 1 or a pharmaceutically acceptable salt thereof and a pharmaceutically acceptable diluent or carrier.

* * * * *